US010363079B2

(12) United States Patent
Vacha et al.

(10) Patent No.: US 10,363,079 B2
(45) Date of Patent: Jul. 30, 2019

(54) ELECTROSURGICAL METHOD AND APPARATUS WITH VARYING STIFFNESS CAPTURE COMPONENTS

(71) Applicant: COVIDIEN AG, Minneapolis, MN (US)

(72) Inventors: John F. Vacha, South Boston, MA (US); Douglas M. Macarthur, Acton, MA (US); Albert Solbjor, Waltham, MA (US)

(73) Assignee: Medtronic Inc., Minneapolis, MN (US)

( * ) Notice: Subject to any disclaimer, the term of this patent is extended or adjusted under 35 U.S.C. 154(b) by 246 days.

(21) Appl. No.: 15/235,891

(22) Filed: Aug. 12, 2016

(65) Prior Publication Data

US 2017/0095286 A1  Apr. 6, 2017

Related U.S. Application Data

(60) Provisional application No. 62/204,807, filed on Aug. 13, 2015, provisional application No. 62/204,836, filed on Aug. 13, 2015.

(51) Int. Cl.
*A61B 17/221* (2006.01)
*A61B 18/00* (2006.01)
(Continued)

(52) U.S. Cl.
CPC .......... *A61B 18/00* (2013.01); *A61B 10/0266* (2013.01); *A61B 17/221* (2013.01);
(Continued)

(58) Field of Classification Search
CPC ............. A61B 10/0266; A61B 17/221; A61B 17/32056; A61B 2017/2212; A61B 2017/2215; A61B 2017/2217
See application file for complete search history.

(56) References Cited

U.S. PATENT DOCUMENTS 2,032,860 A    3/1936  Wappler
3,955,578 A    5/1976  Chamness et al.
(Continued)

FOREIGN PATENT DOCUMENTS

DE    19528440    2/1997
WO    2014105271   7/2014
(Continued)

OTHER PUBLICATIONS

Stereotactic Breast Biopsy: Its History, Its Present, and Its Future, F. Burbank, M.D., The American Surgeon, Feb. 1996, vol. 62, pp. 128-150.
(Continued)

*Primary Examiner* — Joseph A Stoklosa
*Assistant Examiner* — Catherine Premraj
(74) *Attorney, Agent, or Firm* — Patterson, Thuente Pedersen, P.A.

(57) ABSTRACT

An electrosurgical apparatus and method for cutting and resecting a tissue volume is described. The apparatus includes one or more electrosurgical filaments and capture components deployable by forward extension at or near a forward tip of an elongated shaft of the apparatus to form an elliptical path that defines, with the other capture components, a spheroidal receptacle configured to surround a tissue volume for resection. The elliptical path is formable by a first extension followed by a second extension, said first extension having a first axial component and a radial expansion component, and said second extension having a second axial component and a radial contraction component, where at least one of the capture components is of varying stiffness.

30 Claims, 29 Drawing Sheets

(51) Int. Cl.
*A61B 18/12* (2006.01)
*A61B 18/18* (2006.01)
*A61B 10/02* (2006.01)
*A61B 18/04* (2006.01)
*A61B 18/14* (2006.01)

(52) U.S. Cl.
CPC ............ *A61B 18/042* (2013.01); *A61B 18/12* (2013.01); *A61B 18/148* (2013.01); *A61B 18/149* (2013.01); *A61B 18/18* (2013.01); *A61B 18/1206* (2013.01); *A61B 2017/2215* (2013.01); *A61B 2018/00005* (2013.01); *A61B 2018/00267* (2013.01); *A61B 2018/00333* (2013.01); *A61B 2018/00577* (2013.01); *A61B 2018/00601* (2013.01); *A61B 2018/00625* (2013.01); *A61B 2018/00702* (2013.01); *A61B 2018/00767* (2013.01); *A61B 2018/00779* (2013.01); *A61B 2018/00988* (2013.01); *A61B 2018/1213* (2013.01); *A61B 2018/1266* (2013.01); *A61B 2218/007* (2013.01)

(56) References Cited

U.S. PATENT DOCUMENTS

| | | | |
|---|---|---|---|
| 4,202,338 | A | 5/1980 | Bitrolf |
| 4,311,143 | A | 1/1982 | Komiya |
| 4,362,160 | A | 12/1982 | Hiltebrandt |
| 5,925,044 | A | 7/1999 | Hofmann et al. |
| 6,296,639 | B1 | 10/2001 | Truckai et al. |
| 6,331,166 | B1 | 12/2001 | Burbank et al. |
| 6,663,626 | B2 | 12/2003 | Truckai et al. |
| 6,913,579 | B2 | 7/2005 | Truckai et al. |
| 7,044,956 | B2 | 5/2006 | Vetter et al. |
| 7,198,626 | B2 | 4/2007 | Lee et al. |
| 7,615,013 | B2 | 11/2009 | Clifford et al. |
| 7,625,347 | B2 | 12/2009 | Burbank et al. |
| 7,819,819 | B2 | 10/2010 | Quick et al. |
| 8,066,727 | B2 | 11/2011 | Vetter et al. |
| 8,292,822 | B2 | 10/2012 | Fulton et al. |
| 8,460,204 | B2 | 6/2013 | Quick et al. |
| 8,636,734 | B2 | 1/2014 | Burbank et al. |
| 8,992,441 | B2 | 3/2015 | Vetter et al. |
| 9,039,633 | B2 | 5/2015 | Vetter et al. |
| 9,044,215 | B2 | 6/2015 | Shabaz et al. |
| 9,155,527 | B2 | 10/2015 | Vetter et al. |
| 9,204,866 | B2 | 12/2015 | Shabaz et al. |
| 9,216,012 | B2 | 12/2015 | Burbank et al. |
| 9,259,211 | B2 | 2/2016 | Vetter et al. |
| 2001/0047169 | A1 | 11/2001 | McGuckin et al. |
| 2002/0072739 | A1 | 6/2002 | Lee et al. |
| 2003/0225419 | A1* | 12/2003 | Lippitt ............ A61B 17/221 606/127 |
| 2009/0259223 | A1* | 10/2009 | Eggers ............ A61B 18/1402 606/45 |
| 2012/0035503 | A1 | 2/2012 | Vetter et al. |
| 2013/0345739 | A1* | 12/2013 | Brady ............ A61B 17/221 606/200 |
| 2014/0128709 | A1* | 5/2014 | Kordis ............ A61B 5/0422 600/375 |
| 2014/0276911 | A1 | 9/2014 | Smith et al. |

FOREIGN PATENT DOCUMENTS

| | | |
|---|---|---|
| WO | 2015026979 | 2/2015 |
| WO | 2015142674 | 3/2015 |

OTHER PUBLICATIONS

International Search Report and Written Opinion PCT/US 16/46768 dated Oct. 28, 2016, 13 pages.

* cited by examiner

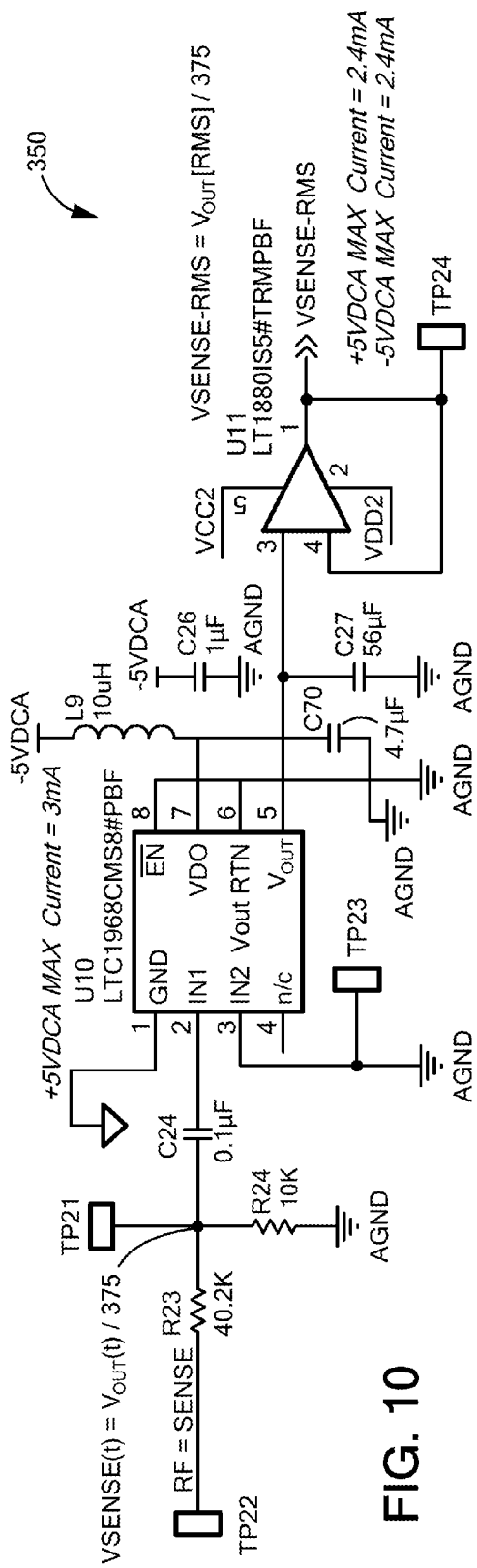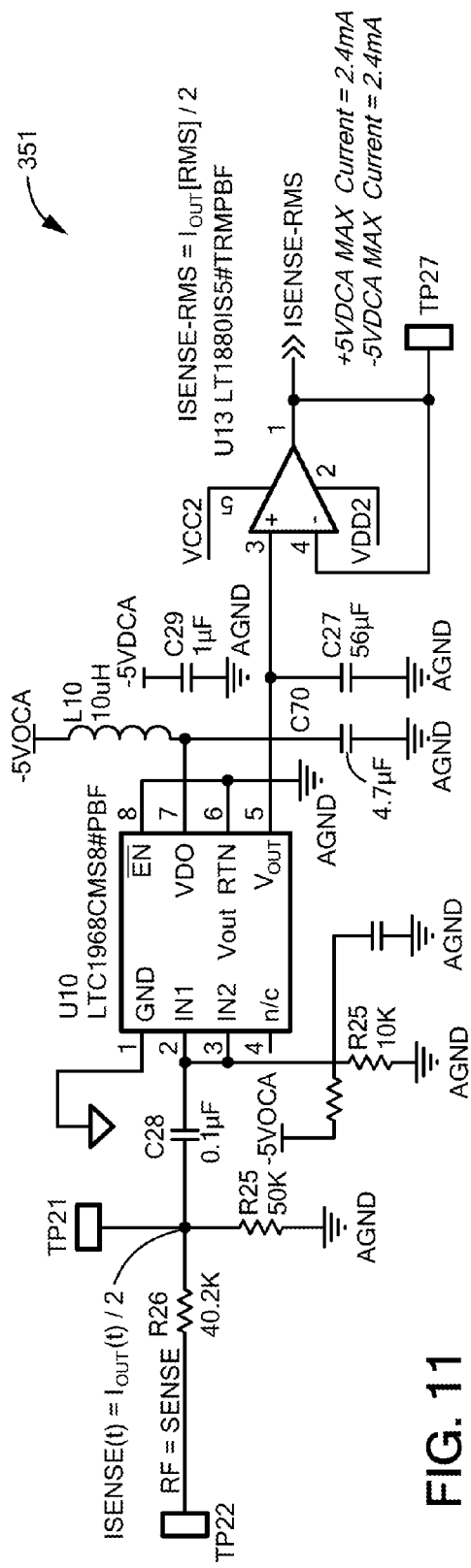
FIG. 10
FIG. 11

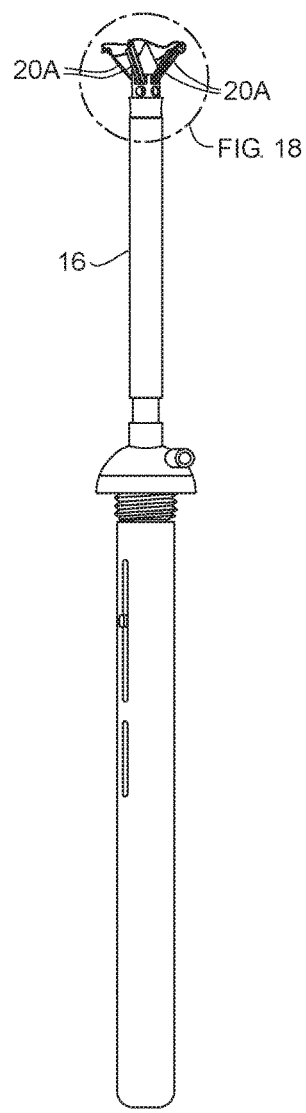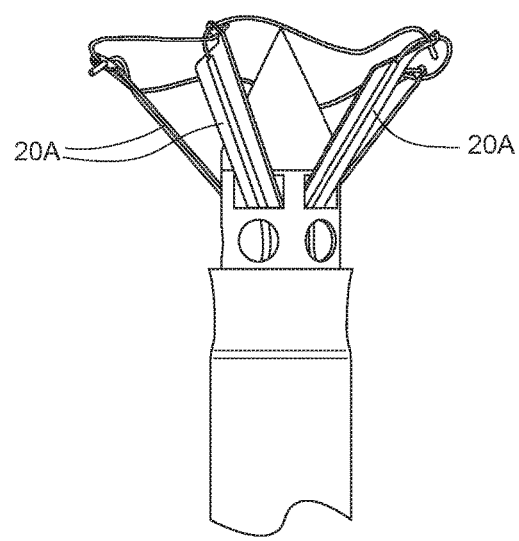
FIG. 17
FIG. 18

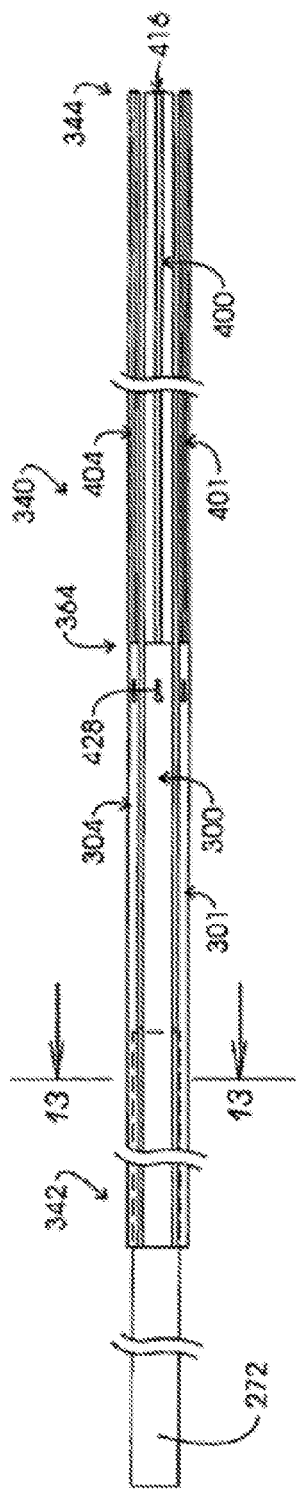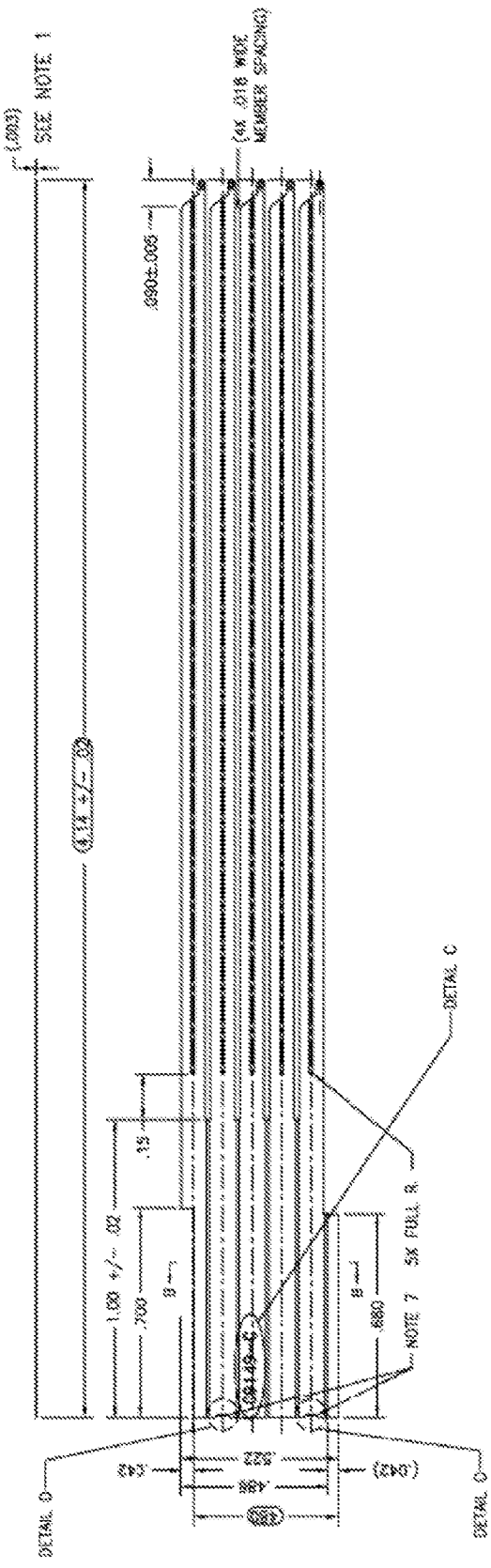
FIG. 25A
FIG. 25B

400

```
┌─────────────────────────────────────────────────────────────────┐
│   Provide a electrosurgical instrument having capture components with │
│       varying stiffness along their length of extension      402 │
└─────────────────────────────────────────────────────────────────┘
                                │
                                ▼
┌─────────────────────────────────────────────────────────────────┐
│  Energize one or more electrosurgical filaments, coupled to leading edges of │
│    the capture components to form a cutting plane, with high frequency │
│            electrical energy by a power generator          404  │
└─────────────────────────────────────────────────────────────────┘
                                │
                                ▼
┌─────────────────────────────────────────────────────────────────┐
│  Extend each of the plurality of capture components and the one or more │
│  electrosurgical filaments by forward extension at or near a forward tip of an │
│  elongated shaft of the apparatus to form an elliptical path that defines, with │
│   the other capture components, a spheroidal receptacle configured to │
│             surround a tissue volume for resection       406    │
└─────────────────────────────────────────────────────────────────┘
```

FIG. 36

ELECTROSURGICAL METHOD AND APPARATUS WITH VARYING STIFFNESS CAPTURE COMPONENTS

CROSS-REFERENCE TO RELATED APPLICATIONS

This application claims the benefit of U.S. Provisional Application No. 62/204,807 filed Aug. 13, 2015, and entitled "ELECTROSURGICAL GENERATOR AND METHODS" and U.S. Provisional Application No. 62/204,836 filed Aug. 13, 2015, and entitled "ELECTROSURGICAL METHOD AND APPARATUS WITH VARYING STIFFNESS CAPTURE COMPONENTS", both of which applications are incorporated herein by reference in their entireties.

STATEMENT REGARDING FEDERALLY SPONSORED RESEARCH

Not Applicable.

FIELD

This disclosure relates generally to electrosurgical apparatus for cutting and resecting a tissue volume and, more particularly to deployable apparatus to define a spheroidal receptacle configured to surround a tissue volume for resection.

BACKGROUND

Existing electrosurgical devices allow for the access and resection of target tissues, in some instances, up to 20-millimeter wide, in biopsies and other diagnostics usages. One class of such devices has flexible struts and a cutting cable that cooperatively extend from the tip of a wand-like electrosurgical apparatus to form a capture receptacle that surrounds a target tissue. The struts are finger-like capture components shaped somewhat as elongated thin leafs that carry the cutting cable at their leading edges. When energized with high-frequency electrical energy, the cutting cable establishes an electrosurgical cutting arc that allows the struts and cutting cable to extend through, by ablation of the contacted tissues, the tissue mass to surround the target tissue.

There is a benefit to electro-surgically resect larger volumes of tissues in a minimally-invasive manner. There is a further benefit in resecting such volumes in a uniform and spheroid geometry.

SUMMARY

The present disclosure provides an electrosurgical device that can access and surgically resect, in a minimally-invasive manner, target tissues (e.g., breast lesions) that are at least 30 millimeters in diametric sized. In addition, the resection is spheroidal in shape. To this end, the present disclosure enables an electrosurgical treatment device, e.g., for electrosurgical excision of small- and large-sized tumors and tissues.

To resect larger volumes of target tissues, struts of the exemplified device are further elongated to form a larger-volume receptacle for the capture of the target tissue. In addition, the thickness of the struts is also increased, in some instances, to maintain a same or similar stiffness property of the struts for a longer structure. Particular surprising and advantageous features of the described technology include the struts having varying mechanical stiffness along its length of extension, including a first stiffness at a first extension section corresponding to the strut's initial deployment from the wand apparatus and a second stiffness at a second extension section corresponding, to its final capture position—this strut structure beneficially yielding a wand performance with a greater receptacle diameter size and a more uniform spheroid shape. The struts are characterized as having a stiffer forward region that precedes a more flexible middle region. The stiffer forward region, in some embodiments, has a generally uniform and wider section (as compared to the middle region), which allows for the extendable deployment of the longer struts at their intended trajectories, i.e., outward from the central axis of the wand.

Specifically exemplified herein is a strut design with concave regions to form the stiffer forward region and the more flexible middle region. The exemplified struts for a 30-mm wide maximum diameter capture device have an initial full-width section that is about 0.55 inch long and about 0.120 inch wide, which transitions to a width about 0.051 inch wide at the thinnest section of the middle region. The middle region in the exemplified struts has a length of about 1.450 inches. The exemplified struts are made of medical-grade 17-7 PH, Condition C, Stainless Steel and are 4 mils thick (i.e., 0.004 inch), which provides equivalent stiffness to existing smaller-sized electrosurgical devices, e.g., 10-mm, 12-mm, 15-mm, and 20-mm devices.

The Examples included herein demonstrate, among other things, that spheroid shaped tissues at least 30 mm in width, can be electro-surgically resected, in a minimally-invasive manner, from a tissue mass, for example, to provide tissues for the diagnostic sampling of breast abnormalities and/or for histologic examination with partial and/or complete removal of a palpable abnormality, while preserving the lesion/tissue architecture in the samples.

Further exemplified herein is a strut design with concave regions for an electrosurgical device having between 10 and 20 mm wide maximum diameter, e.g., 10 mm, 12 mm, 15 mm, and 20 mm, configured to electro-surgically ablate through a tissue mass in an elliptical or arcuate path to form a spheroidal shaped tissue for capture and resection.

In one aspect, an electrosurgical apparatus for cutting and resecting a tissue volume is disclosed. The apparatus includes one or more electrosurgical filaments (e.g., tungsten alloy filament) and a plurality of capture components (e.g., elongated stainless-steel leafs). The capture components are coupled, at their leading edges, to the electrosurgical filaments to define a cutting plane. The plurality of capture components and one or more electrosurgical filaments are deployable by forward extension at or near a forward tip of an elongated shaft of the apparatus to form an elliptical path that defines, with the other capture components, a spheroidal receptacle configured to surround a tissue volume for resection. The elliptical path is formable by a first extension followed by a second extension, this first extension having a first axial component and a radial expansion component, and this second extension having a second axial component and a radial contraction component, wherein at least one of the plurality of capture components is of varying stiffness, including i) a first stiffness corresponding to the first extension and ii) a second stiffness corresponding to the second extension, and wherein the first stiffness is greater than the second stiffness.

In some embodiments, the first extension corresponds to a first width section of a capture component of the plurality of capture components, and the second extension corresponds to a second width section capture component of the plurality of the capture components, wherein the first width section has a first width and the second width section has a second width, and wherein the first width is greater than the second width. In some embodiments, the first width section is at least 0.550 inch in length.

In some embodiments, a portion of the second width section forms a concave shape.

In some embodiments, a portion of the first width section has a uniform width.

In some embodiments, the first extension, having the first axial component and the radial expansion component, results from the plurality of capture components and one or more electrosurgical filaments being extendable at the same travel rate. In some embodiments, the first extension further results from i) the plurality of capture components being extendable at a first travel rate and the one or more cutting electrodes being extendable at a second travel rate, the first travel rate being greater than the second travel rate.

In some embodiments, the second extension, having the second axial component and the radial contraction component, results from i) the plurality of capture components being extendable at a first travel rate and the one or more electrosurgical filaments being extendable at a second travel rate, the first travel rate being greater than the second travel rate.

In some embodiments, the second extension occurs after a deployment position along the elliptical path corresponding to a maximum diametric size of the apparatus.

In some embodiments, each of the plurality of capture components is at least 0.004 inch thick.

In some embodiments, the second extension, having the second axial component and the radial contraction component, forms a maximum capture diameter of the apparatus.

In some embodiments, the maximum capture diameter is about 30 millimeters.

In some embodiments, the maximum capture diameter is greater than 30 millimeters.

In some embodiments, the maximum capture diameter is selected from the group consisting of about 10 millimeters, about 12 millimeters, about 15 millimeters, and about 20 millimeters.

In some embodiments, the plurality capture components are connected together via a base as a single structure.

In some embodiments, each of the plurality of capture components couples to a electrosurgical filament of the one or more electrosurgical filaments via an eyelet, the eyelet comprising a low-friction coating.

In another aspect, a method for electrosurgical cutting and resecting of a tissue volume is disclosed. The method includes providing an electrosurgical instrument, in which the instrument includes one or more electrosurgical filaments (e.g., tungsten alloy filaments) and a plurality of capture components (e.g., elongated stainless-steel leafs). The capture components are coupled, at their leading edges, to the one or more electrosurgical filaments to define a cutting plane.

The method further includes energizing the one or more electrosurgical filaments with high frequency electrical energy.

The method further includes extending each of the plurality of capture components and the one or more electrosurgical filaments by forward extension at or near a forward tip of an elongated shaft of the apparatus to form an elliptical path that defines, with the other capture components, a spheroidal receptacle configured to surround a tissue volume for resection, wherein the elliptical path is formable by a first extension followed by a second extension, this first extension having a first axial component and a radial expansion component, and this second extension having a second axial component and a radial contraction component, wherein at least one of the plurality of capture components is of varying stiffness, including i) a first stiffness corresponding to the first extension and ii) a second stiffness corresponding to the second extension, and wherein the first stiffness is greater than the second stiffness.

In some embodiments, the first extension corresponds to a first width section of a capture component of the plurality of capture components, and the second extension corresponds to a second width section of the capture component of the plurality of capture components, wherein the first width section has a first width and the second width section has a second width, and wherein the first width is greater than the second width. In some embodiments, the first width section is at least 0.550 inch in length.

In some embodiments, a part of the second width section forms a concave shape.

In some embodiments, a part of the first width section has uniform width.

In some embodiments, the first extension, having the first axial component and the radial expansion component, results from the plurality of capture components and one or more electrosurgical filaments being extendable at the same travel rate. In some embodiments, the first extension further results from i) the plurality of capture components being extendable at a first travel rate and the one or more cutting electrodes being extendable at a second travel rate, the first travel rate being greater than the second travel rate.

In some embodiments, the second extension, having the second axial component and the radial contraction component, results from i) the plurality of capture components being extendable at a first travel rate and the one or more electrosurgical filaments being extendable at a second travel rate, the first travel rate being greater than the second travel rate. In some embodiments, the second extension occurs after a deployment position along the elliptical path corresponding to a maximum diametric size of the apparatus.

In some embodiments, each of the plurality of capture components is at least 0.004 inch thick.

In some embodiments, the second extension, having the second axial component and the radial contraction component, forms a maximum capture diameter of the apparatus. In some embodiments, the maximum capture diameter is about 30 millimeters. In some embodiments, the maximum capture diameter is greater than 30 millimeters. In some embodiments, the maximum capture diameter is selected from the group consisting of about 10 millimeters, about 12 millimeters, about 15 millimeters, and about 20 millimeters.

In some embodiments, the plurality capture components are connected together via a base as a single structure.

In some embodiments, each of the plurality of capture components couples to a electrosurgical filament of the one or more electrosurgical filaments via an eyelet, the eyelet comprising a low-friction coating.

In another aspect, an electrosurgical apparatus is disclosed. The apparatus includes one or more electrosurgical filaments (e.g., tungsten alloy filaments) and a plurality of capture components (e.g., elongated stainless-steel leafs), which are coupled, at their leading edges, to the one or more electrosurgical filaments to define a cutting plane. The plurality of capture components and one or more electrosurgical filaments are deployable by forward extension at or near a forward tip of an elongated shaft of the apparatus to form an elliptical path that defines, with the other capture components, a spheroidal receptacle configured to surround a tissue volume for resection, wherein the elliptical path is formable by a first extension followed by a second extension, the first extension having a first axial component and a radial expansion component, and the second extension having a second axial component and a radial contraction component, and wherein the second extension comprises a portion of one or more concave regions. In some embodiments, the concave regions define an hourglass shape member for each of the plurality of capture components.

BRIEF DESCRIPTION OF THE DRAWINGS

FIGS. 10 and 11 illustrate example converter circuits employed to convert instantaneous current and voltage measurements to average current and voltage measurements;

FIG. 17 shows a probe of an example electrosurgical apparatus with capture components at a stage in its deployment, the capture component having a uniform width;

FIG. 18 depicts a detailed view of the capture components of FIG. 17;

FIGS. 25A and 25B are views of an example capture component assembly configured for pre-assembly into the probe of FIG. 16;

FIG. 36 is diagram of a method of operating an electrosurgical instrument according to an illustrative embodiment.

DETAILED DESCRIPTION

Figure 1:
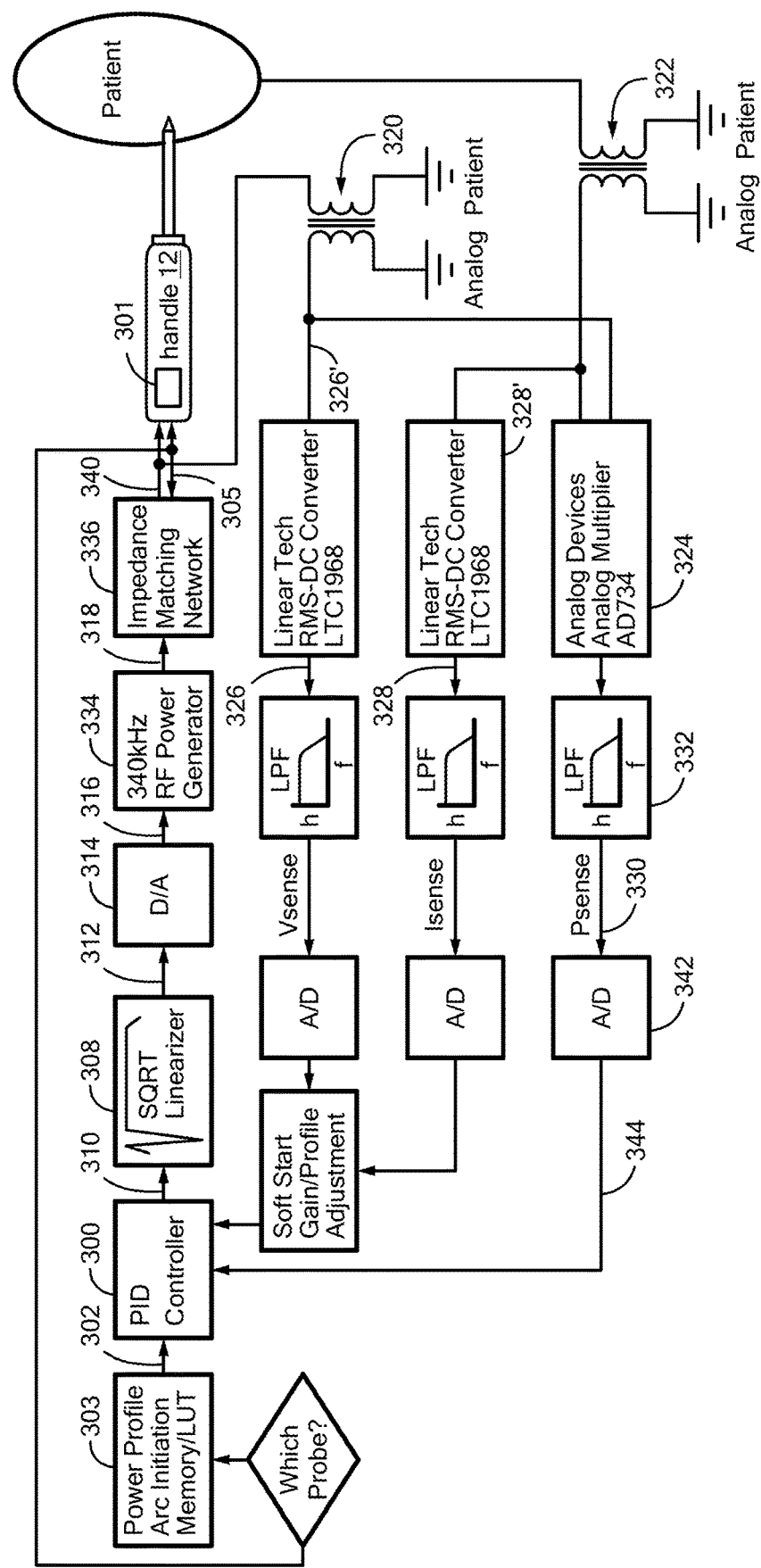
FIG. 1 is an illustration of an example power control system in accordance with an embodiment.

The disclosed technology includes an RF power generator for an electrosurgical instrument configured to create a uniform cutting arc. In certain embodiments, the exemplified RF generator enables the maintenance of substantially uniform power density of cutting arcs generated by electrosurgical instruments for the resection of tissue up to, at least, 30 millimeters in diametric size (e.g., 12 mm, 15 mm, 20 mm, or 30 mm). Electrosurgical resection of volumes of tissues at least 30-mm wide is beneficial and, in some embodiments, essential in the excision of tissues, e.g., tumors and other unwarranted tissues, beyond diagnostics purposes, e.g., as a therapy. Specifically exemplified herein is a strut design with varying stiffness along its length of extension. Struts are finger-like appendages located inside a probe portion of the electrosurgical apparatus that carry the cutting cable through the deployment process. The struts form a part of the basket-like receptacle when extended from a stowed position to a deployed position.

In some embodiments, each of the struts forms a concave region that provides a wider forward region followed by narrower middle region to form a shape resembling an elongated hourglass. Alternatively to, or in combination with, the struts having different widths, the struts may be made of two or more materials having different elastic modulus properties (e.g., Young's modulus) to vary the strut's stiffness along its length of extension. Similarly, in addition to having different widths, the thickness of the struts may also be varied along the length of the strut's extension to vary the stiffness of the struts.

Described herein is an electrosurgical wand for the resection and/or excision of tissue volumes at least about 30 millimeters wide. A strut exemplified herein has a full width initial section and a narrower middle section. The full width initial section (also referred to herein as the "forward section" of the strut) of the strut forms a stiff active section, enabling the strut to deploy at an intended trajectory (e.g., about 45 degrees) outward from the central axis of the wand device. The narrower middle section corresponds to an extension region that follows the full width initial portion. The narrow section is observed to induce a rounder bend as the basket closes. The full width initial section is stiffer than the narrow middle section. In some embodiments, the full width initial section is the stiffest section of the struts. The exemplified design yields a wand performance with a maximum basket diameter and uniform shape.

In an exemplified embodiment, the full width initial section is about 0.550 inch long and about 0.120 inch wide. The full width section transitions to the narrower middle section, in some embodiments, about 0.051 inch wide. In the exemplified embodiment, the struts is about 4 mils thick (0.004 inch), which has a stiffness similar to struts of certain 10-mm to 20-mm devices that are 3 mils thick (0.003 inch) in which the struts have a uniform cross-section and are about 0.080 inch wide. The exemplified struts are made of medical-grade 17-7 PH, Condition C, Stainless Steel and are about 4 mils thick (0.004 inch).

Larger diametric-size capture components can be employed, in some embodiments, by increasing the length of the exemplified struts while maintaining equivalent stiffness of the struts in the middle region. For equivalent strut stiffness, the struts may be scaled consistent with beam theory in which the stiffness is linearly related to the width of the struts, cubically related to the thickness of the struts, and cubically related to the length of the struts, according to Equation 1.

$$\text{Stiffness} = f[b, h^3, l^3], \quad \text{(Equation 1)}$$

where b is the width of a strut, h is the thickness of the strut, and l is the length of the strut. As the resection volume size increases, higher output power is necessary to cut through more tissue during the ablation. To this end, the higher power output, in view of the variability in the electrical characteristics of the tissue, increases the likelihood of stalls or overcurrent/overpower events that can result in an incomplete deployment of the instrument. The disclosed technology provides, among other things, a measurement of the average real-power delivered to the cutting arc which allows for the maintenance of a more uniform real-power delivered throughout the exposed length of the cutting filament. In addition, the disclosed technology further provides for the tuning of the output power to match the average tissue impedance of the target tissue. These features reduce, among other things, the likelihood of occurrences of localized power fluctuations that can destabilize the control, damage the tissues in unintended ways, or damage the instrument.

The disclosed technology includes the use of improved output sensing signals as feedback for an improved power control scheme. In some embodiments, the control system maintains uniform real power density throughout the exposed length of the wand cutting cable. In simpler terms, the power is raised as the cutting cable length increases and then the power is reduced as the cutting cable length is reduced during the pursing of the basket close.

FIG. 1 is an illustration of an example power control system in accordance with an embodiment. The disclosed technology includes a feedback control system that works to regulate the power delivered to the cutting electrode of the excision device probe. Since the goal of the device is to remove a tissue sample for analysis by pathology, the tissue captured by the probe cannot be damaged by the act of removal through RF ablation. It is this requirement that dictates the optimum output power level: too much power used for cutting destroys the sample, too little power delivered results in incomplete tissue capture or small sample size. Since the exposed length of the cutting electrode changes according to deployment time, the total power delivered to the cutting electrode must change in order to preserve the power density along the length of the electrode wire.

Although it is desirable to deliver a constant power density to the cutting electrode, there are other factors that modify the optimum power delivery function, P(t). First, in order to maintain minimal cutting mechanical resistance (electrode drag), a plasma must exist around the cutting electrode. This plasma localizes the heat around the cutting electrode such that the local temperature around the electrode wire is high enough to vaporize the adjacent tissue, thus reducing the mechanical resistance of cutting. Reduction in mechanical drag tends to produce a more-spherically shaped sample and also tends to increase sample size. Another benefit of the presence of the plasma is that the severed blood vessels are more likely to be cauterized, therefore reducing post-surgery swelling. Second, the struts of the probe are capacitively coupled to the surrounding tissue. This parasitic capacitance results in power loss to the cutting electrode through leakage to the surrounding tissue. Third, and last, at the end of the capture cycle as the struts purse together, the power delivered must be great enough to overcome a gap remaining as the electrode circumference reduces to a minimum value (but not zero). To fully detach the tissue sample, the power must be great enough to vaporize all of the tissue within the plane of the remaining gap. Due to the necessity of plasma (or arc) initiation, the leakage associated with the strut capacitance, and tissue detachment power, the power delivery function must be modified to account for these factors.

During the arc initiation phase of operation, for a short time (e.g., less than 500 ms), the controller outputs a power level that is much higher than what is considered ideal for cutting in order to form plasma around the electrode. During this period, the intracellular and extracellular fluid adjacent to the electrode accumulate heat to the point of vaporization. This vapor ionizes and forms a conductive plasma. As the plasma forms around the electrode, it contributes to the electrical impedance seen by the RF generator (e.g., adds resistance and capacitance). Plasma has an electrical characteristic commonly known as negative impedance, although this term is a misnomer. Because the conductivity of the plasma depends on the density of ions within the plasma, an increase in current causes an increase in heat, which in turn creates more ions, resulting in a drop in voltage across the arc. This nonlinear behavior complicates the control of the power delivery, especially during the transition between no-arc and arc-present states. To help stabilize the control system during this transition, the controller employs a "soft-start" state. The soft-start algorithm performs two functions simultaneously: 1) exponentially decays the power delivered from arc initiation to cutting phases and 2) asymptotically increases the gains of the PID controller such that the gains are gradually increased to reduce power delivery error during the cutting phase.

As the controller transitions to the cutting state, the power output gradually approaches a profile that is designed for the specific probe in use. As previously mentioned, to preserve tissue sample integrity it is desirable to keep a substantially constant power density along the length of the electrode wire throughout the capture cycle. However, as also previously mentioned, the probe strut capacitance contributes to leakage of power to surrounding tissue and the power delivered at the end of the capture cycle must also be elevated from ideal cutting level to fully detach the tissue sample. Starting with the function of exposed electrode length alone, the power delivery function can be approximated based on previously compiled empirical evidence. After that, the function may or may not be modified according to performance trade-offs in order to derive the desired power outputs (i.e., power profiles, or power curves) 302. To aid the design of the optimum power profile for a given probe size and geometry, the disclosed technology may employ an interpolation scheme where the user enters information about the desired power delivery function in phases and segments, then selects from a list the type of mathematical interpolation desired. As the fields for the information are changed by the user, the system modifies a proposed power output profile in the form of a graph. The user can then "massage" the data iteratively until the power profile has been optimized. The power output specifications that may be set by the user are as follows: RF generator program voltage during arc initiation, duration of arc initiation phase, soft start specification in the form of time constants (e.g., analogous to half-life), 4-point power profile definition (e.g., time and power), and type of interpolation scheme (e.g., Piecewise Linear, Spline, Cubic Hermite, or Lagrange).

Power control software, the RF generator, and a data acquisition board in conjunction form a feedback control system which works to regulate the total power delivered to the cutting electrode (e.g., handle 12). Specifically, in certain embodiments, the software runs a 1 kHz PID-type controller 300. The main sensor of the feedback loop is an analog multiplier 324 that is located on the RF generator. The RF generator contains two transformers 320, 322 connected to sample the output voltage and the output current delivered to the cutting electrode. The instantaneous power is the multiplication of the current and the voltage signals. However, the instantaneous power is a time varying function (due to reflections) that can be positive (delivered) and negative (reflected). In certain embodiments, it is desirable to control the average power delivered, so the output of the analog multiplier is low-pass filtered by low-pass filter (LPF) 332. This signal (Psense) 330 is sampled by an A/D converter 342 on the data acquisition board and fed into the PID controller, which compares the output power to the programmed power profile 302. The output 310 of the PID controller 300 is used to set the output level of the RF generator. However, since the output of the PID controller is in reference to power, and the control signal of the RF generator (DC-DC-CMD) sets the generator output voltage, a square-root function linearizer 308 may be used in order to avoid non-linearities in the control system. This non-linearity is due to the fact that the output power is proportional to the square of the output voltage and is inversely proportional to the load impedance.

$$P = \frac{V_{RMS}^2}{|Z|} \times \cos(\text{angle } Z)$$ (Equation 1)

The linearizer 308 increases the stability of the control system, resulting in greater precision. Finally, the output power of the RF generator is desensitized to changes in load impedance by the addition of an impedance matching network 336.

The control includes a PID controller 300 that regulates the power delivered to the electrosurgical instrument 12. In some embodiments, the PID controller 300 compares a desired power output reference 302 to a sensor measurement (e.g., 344) of the power delivered. The desired power output 302, in some embodiments, is a part of the forward feedback component that is specific to and tailored for each type (e.g., capture size) of device (e.g., instrument 12). The desired power output 302 is stored, in some embodiments, in memory 303 and includes, in some embodiments, a power output level for the different stages of the power control (e.g., during arc initiation stage, during the initial cutting stage, during the intermediate cutting stage, and during the final cutting stage).

In some embodiments, desired power outputs 302 (referred to alternatively herein as control settings, power profiles, and power curves) are stored in a library of power outputs (e.g., in a look-up table) 303 that is indexed according to probe type. In some embodiments, the desired power output is indexed according to the size of the capture instrument. The probe type, in some embodiments, is determined according to a coding identifier 301 that is housed within each probe for the automatic identification of the instrument.

Wands each have an identifier 301 associated with them which define their type to the controller. This can be accomplished in a number of ways, simplest being the addition of a discrete resistor to each probe size on a signal line monitored by the controller. The identifier 301 may alternatively or additionally include a capacitor and/or an integrated circuit (IC) data module. The controller logic will assign a tuned power output curve to each wand type. Each wand captures a different diameter of tissue and the exposed length of cable at maximum opening is different. A control setting, such as a power curve is optimized for each probe. In some embodiments, use of a power curve optimized for each probe type may be useful to maintain a uniform, or substantially uniform power density throughout the capture. In an embodiment, the discrete power curve 302 may include one or more of an output voltage for arc initiation, an output time for arc initiation, a soft-start output power (e.g., a time constant value) and a power profile definition, referred to alternatively as simply a power profile definition, or power curve (e.g., an n-point curve with each point comprising a time and a power value).

In an embodiment, one or more of the plurality of power profile definitions, or power curves 302 stored in memory 303 has a positive slope (i.e., increasing desired power values) for a first time interval, a substantially zero slope (i.e., substantially constant power values) for a second time interval following the first time interval, and a negative slope (i.e., decreasing power values) for a third time interval following the second time interval. In other embodiments, the negative slope portion of one or more such power curves may be omitted and the power may be maintained at a relatively constant level until the generator is turned off. In some embodiments, each unique wand type may have a corresponding, unique power curve (e.g., unique power values and/or unique power curve shape and/or durations for each power control stage) and, in other embodiments, one or more different wand types may share the same power curve (e.g., same power values and/or same power curve shape and/or durations for each power control stage).

A connector of the handle 12 configured to be received by the RF generator may include a power line, a ground line, and an interface line 305. In operation, the controller may interrogate the instrument to retrieve an identifier signal through the interface line 305, which identifier signal is associated with the instrument type. In an embodiment, the identifier 301 includes a resistor and interrogation includes applying an electric potential to the interface line and measuring a resulting current through the interface line to measure a resistance of the resistor.

Figure 2A:
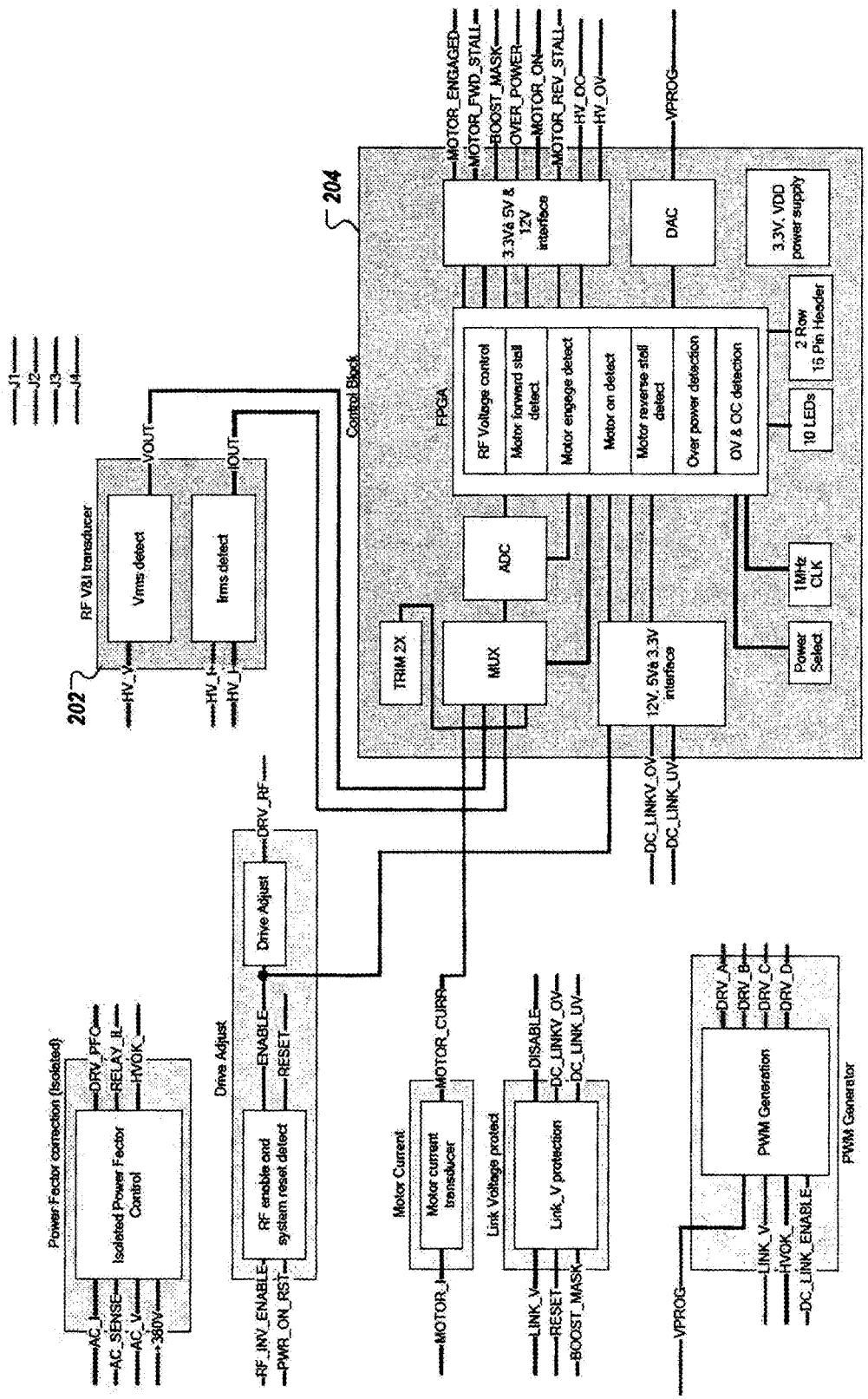
FIGS. 2A through 2D illustrate a drive board and various components therein in accordance with an embodiment.
Figure 2B:
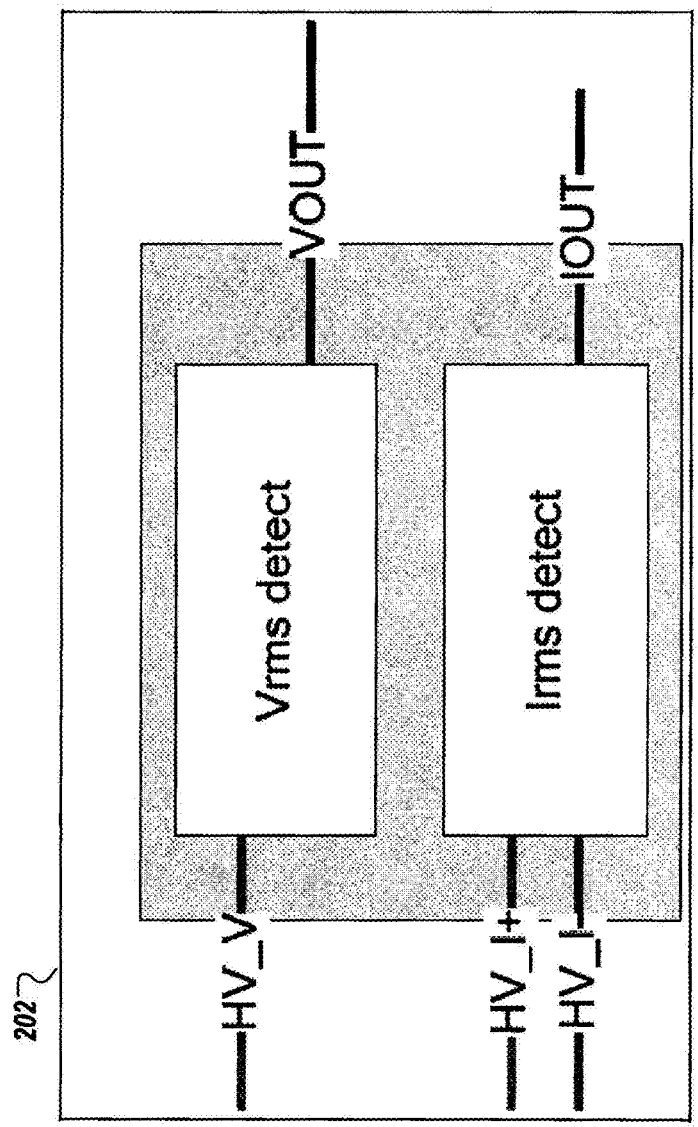

FIG. 2A provides a top level block diagram of a drive board in accordance with an embodiment of the disclosure. The RF V & I transducer 202 takes in the sense signals from the RF output circuitry and generates voltages proportional to the RMS voltage and current as shown in FIG. 2B. The transducer 202 has three inputs $HV_V$, $HV_{I+}$, and $HV_{I-}$. $HV_V$ ranges from 0 to 12V and is the rectified AC output of the RF generator, stepped down by, in certain embodiments, 40:1. $HV_{I+}$ and $HV_{I-}$ are connected to a current transformer with a step down, in certain embodiments, of 200:1. The transducer circuit 202 generates two outputs $V_{OUT}$ and $I_{OUT}$. $V_{OUT}$ is a voltage proportional to the RMS RF voltage, scaled to match the input range of the ADC. Similarly, $I_{OUT}$ is a current proportional to the RMS RF current, scaled to match the input range of the ADC.

Figure 2C:
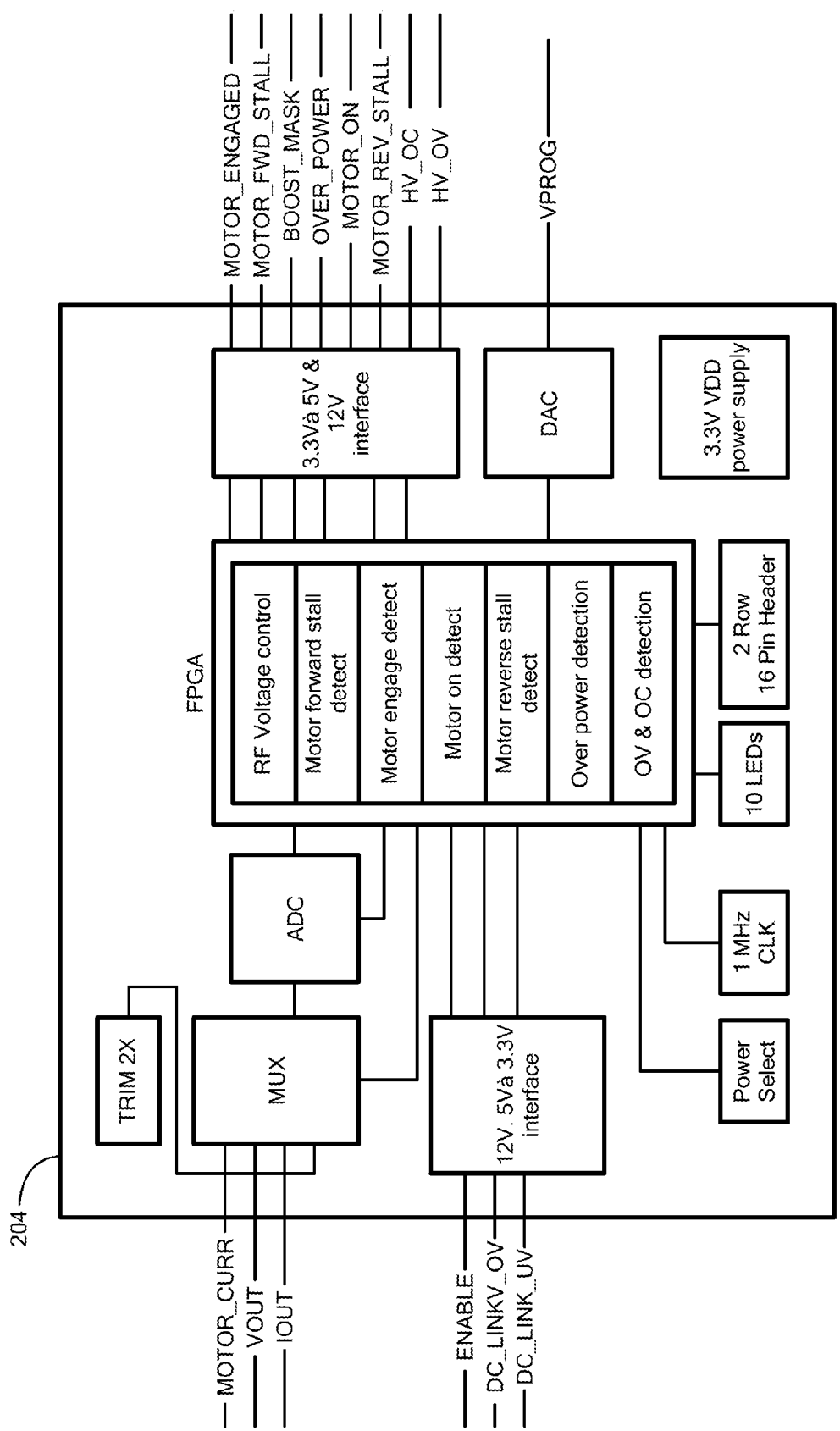
Figure 2D:
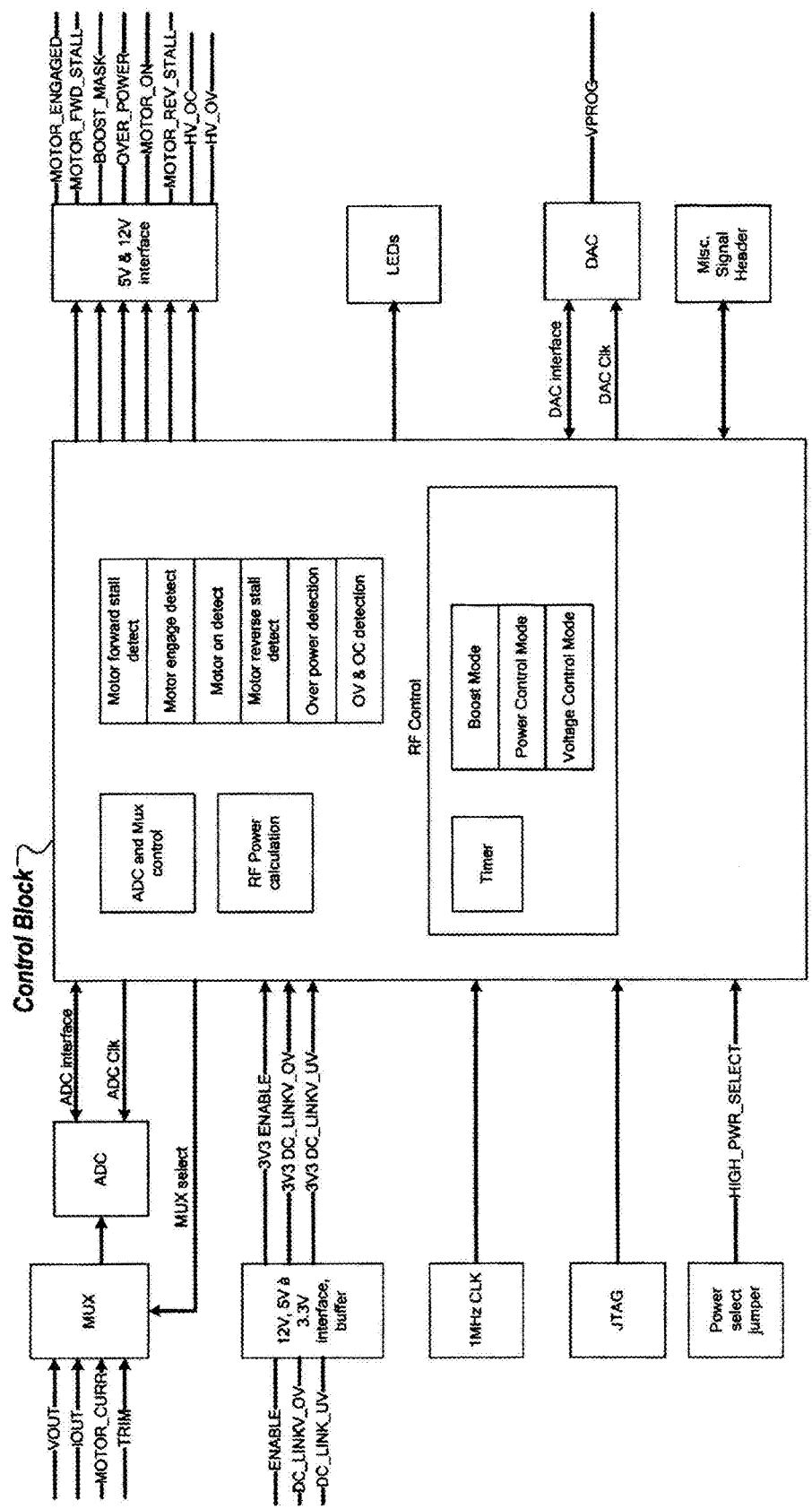

The control block 204 is shown in FIGS. 2A, 2C, and 2D. The control block is responsible for controlling the RF output and monitoring the handset. The control block shown in FIG. 2D differs slightly from that shown in FIGS. 2A and 2C as the control block in FIG. 2D shows additional detail.

The FPGA in the control block performs, in certain embodiments, several top level tasks. These may include RF control, generating motor status signals, and generating high voltage current and voltage errors.

Figure 3:
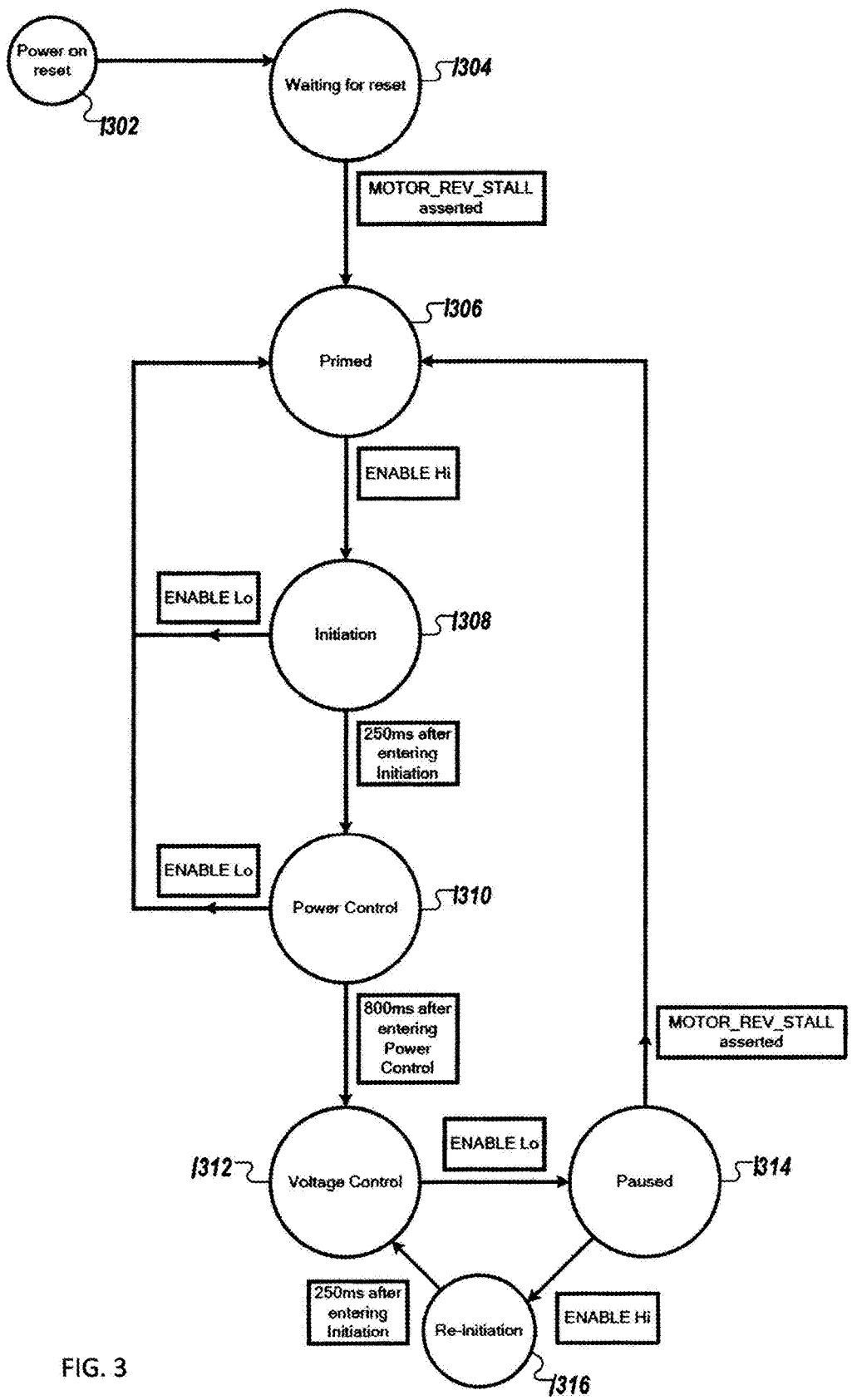
FIG. 3 is an illustration of an example FPGA control scheme.

FIG. 3 is an illustration of an example FPGA control scheme. In step 1302 (power on reset), all registers, etc. are cleared and the FPGA is reset to a known state. This state immediately moves to waiting for reset state 1304. During the waiting for reset state 1304, the FPGA is waiting for the handset to be reset. It detects handset by waiting for MOTOR_REV_STALL to be asserted. When this occurs the FPGA moves to a primed state 1306.

During the primed state 1306, the FPGA is waiting for the ENABLE signal to be asserted. This signals the start of the RF sequence. When the ENABLE signal is detected the FPGA moves to an initiation state 1308.

In the initiation state 308 the FPGA ignites the RF arc by requesting a fixed voltage (e.g., VPROG set to 2.7 V) for a period of time, such as 250 ms. After this period of time (e.g., 250 ms) the FPGA moves to a power control state 1310. If ENABLE goes low then the FPGA returns to waiting for reset state 1304.

In the power control state 1310, for a second period of time (e.g., 800 ms) the FPGA uses a PI control loop to control the output power of the generator. The RF output power is calculated by multiplying together IOUT and VOUT. The target power level can be selected using a jumper attached to the HI_PWR_SELECT pin. The RF power is controlled by changing VPROG, which adjusts the RF voltage. After second period of time (e.g., 800 ms) the FPGA moves to voltage control state 1312. The set point in the voltage control state 1312 is set to be the RF output voltage when the power control state 1310 is left. If ENABLE goes low then the FPGA returns to the waiting for reset state 1304.

The FPGA uses a PI control loop to control the output voltage of the generator. The target voltage is the RF output voltage when the power control state 1310 was exited. The RF voltage is controlled by changing VPROG, which adjusts the RF voltage. If ENABLE goes low then the FPGA moves to the paused state 1314.

In the paused state 1314 the FPGA waits either for the handset to be reset (MOTOR_REV_STALL is asserted) in which case it moves to primed state 1306 or for the capture to be restarted (ENABLE Hi). If this occurs then the FPGA moves to re-initiation state 1316.

In the re-initiation state 1316 the FPGA ignites the RF arc by requesting a set voltage (VPROG set to 2.7 V) for a period of time, such as 250 ms. After this period of time (e.g., 250 ms) the FPGA moves to the voltage control state 1312.

Both the voltage and power control are handled by very similar control loops. Every time through the loop the following occurs: deduct the feedback measurement from the set point, multiply the answer by the control constant, add the answer to the current loop output, and set VOUT equal to the loop output.

In voltage control state 1312, the set point and feedback measurement are both in Vrms and the output is in volts. In power control state 1310 the set point and feedback measurement are both in Watts.

In some embodiments, the FPGA implements only an over current and/or an overpower safety shut down feature and/or provides gate drive signals to a chopper circuit.

Figure 4:
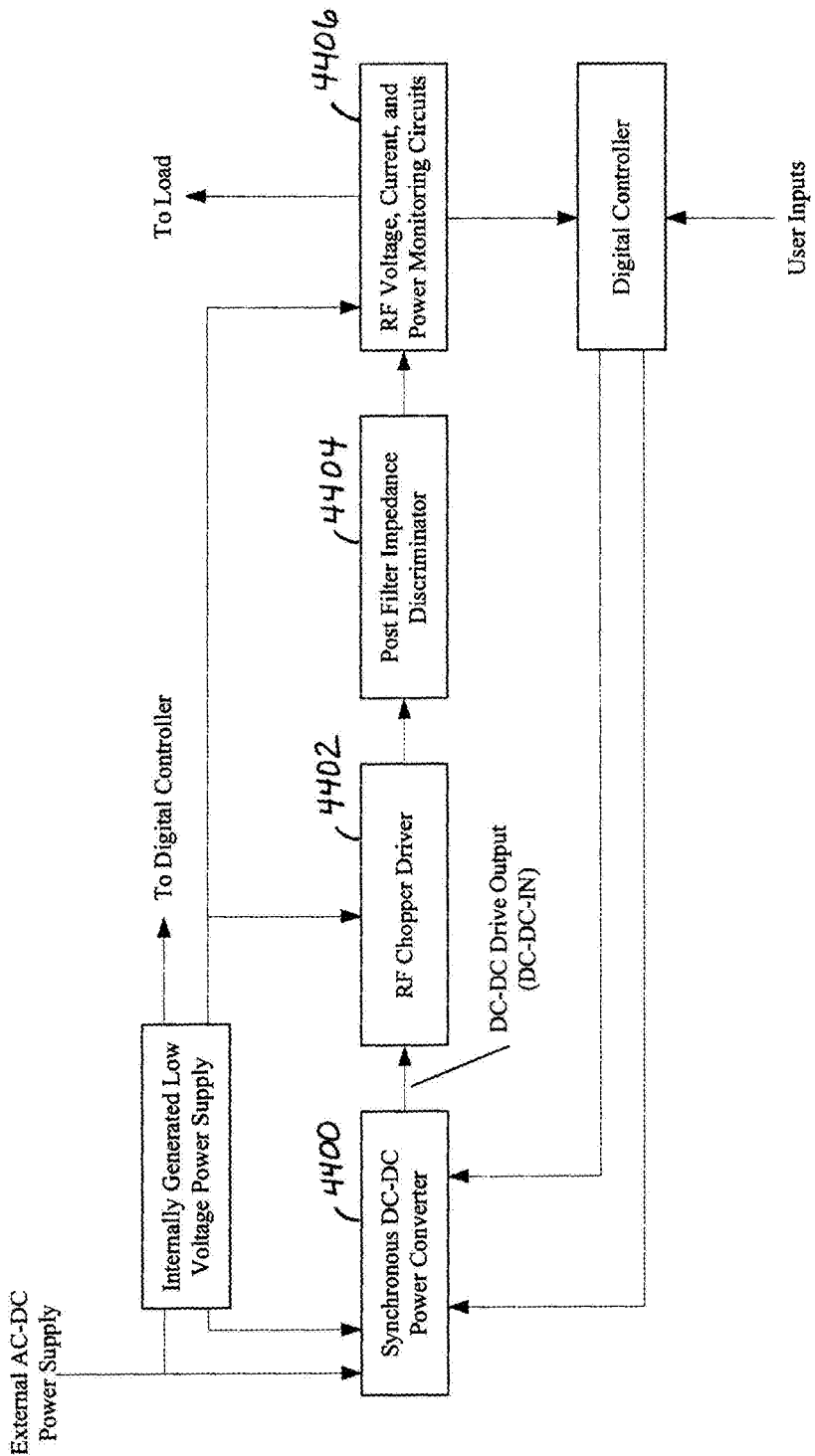
FIG. 4 is an illustration of an RF generator architecture in accordance with an embodiment.

FIG. 4 is an illustration of an RF generator architecture in accordance with an embodiment. A description of synchronous DC-DC power converter 400, RF chopper driver 402, post filter impedance discriminator 404, and RF voltage, current, and average power monitoring circuits 406 is provided below.

Synchronous DC-DC Power Converter

The primary function of the synchronous DC-DC converter 4400 is to generate a DC voltage under the command of the "Digital Controller" produced signal called "DC-DC-CMD." This signal produces an output DC voltage called "DC-DC-IN" which is applied to the RF chopper 4402 transformer's primary. Consequently, the Synchronous DC-DC output voltage modulates the final output RF voltage amplitude at the load.

In certain embodiments, the DC voltage gain is from +10 to +15 (e.g. +14.1 or +12), meaning that a DC analog command voltage from the digital controller (0 VDC to +5 VDC) will create a Synchronous DC-DC output voltage of anywhere from 0 VDC to +60 VDC (upper DC voltage depends upon the externally applied DC voltage from the AC-DC converter shown in FIG. 4). This voltage is applied to the RF Chopper transformer center tapped primary as stated.

The pulse width modulation scheme used to produce the varying DC voltage output is applied using a high voltage half-bridge driver integrated circuit (IC) (e.g., Linear Technology LTC3703). In certain embodiments, this IC has a built-in shutdown bit which completely shut the DC-DC conversion process off and renders a high state impedance at the output. The DC-DC control voltage and shutdown bit are shown in FIG. 4. As mentioned previously, in certain embodiments, the LT half-bridge driver IC is synchronized to a 170 KHz logic level signal to eliminate any beat frequencies between the RF chopper and DC-DC converter stages.

In certain embodiments, a similar subsystem function uses an H-Switch topology otherwise known as a full bridge switch. In other embodiments, a half-bridge topology is used and is driven by a fixed frequency TCXO oscillator at sync-locked at 170 KHz from the "RF Chopper Driver's" oscillator. In certain embodiments, the Synchronous DC-DC Power Converter 4400 incorporates a fused input and a DC current limitation set by a resistor to prevent damage to the converter under excessive converter loading.

RF Chopper Driver

Figure 5:
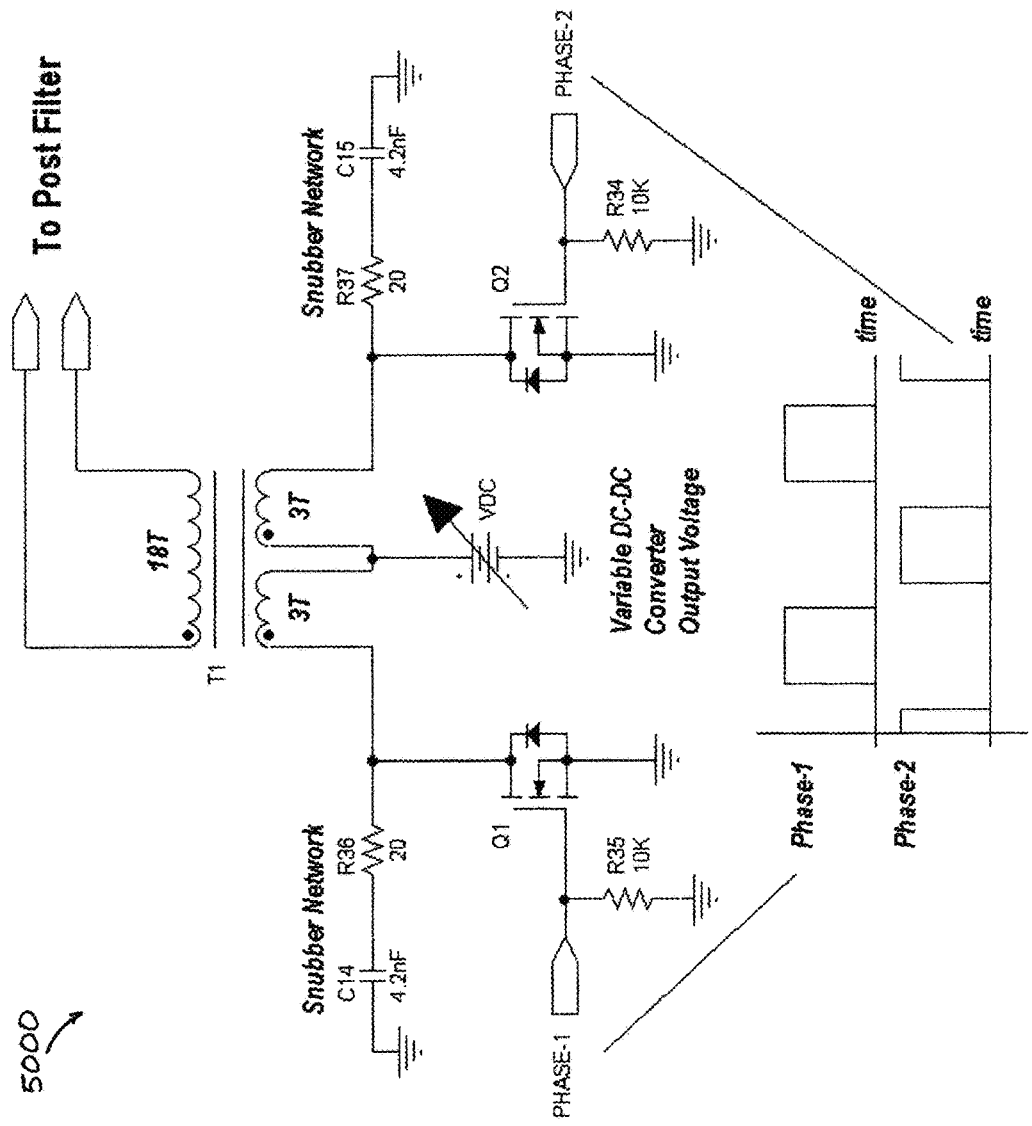
FIG. 5 is an illustration of an example RF chopper driver.

FIG. 5 is an illustration of an example RF chopper driver 5000. In certain embodiments, the RF chopper driver is a push-pull topology as shown in FIG. 5. In general, two complimentary digital voltage level signals alternately switch MOSFETS Q1 and Q2 ON and OFF. This switching action alternately applies a +VDC potential (note polarity of VDC in FIG. 5) from the "Variable DC-DC Converter Output Voltage" to transformer T1's secondary winding. The primary-to-secondary turns ratio for winding is 1:6, hence the alternating +VDC amplifies, by a factor of 6 (e.g., multiply by ±6x), the VDC magnitude AC square wave on the secondary or "To Post Filter" side. The RF chopper logic drive provide a required dead time (e.g., 200 nanoseconds) between alternating pulse drive signals Phase-1 and Phase-2 to insure that both MOSFETS do not turn ON simultaneously and saturate T1's toroid core.

Post Filter Impedance Discriminator

Referring back to FIG. 1, a post-processing filter impedance discriminator circuit is shown as 336 (also shown as 4404 in FIG. 4). The impedance load discriminator circuit 336 normalizes the power delivered to the cutting filament when ablating through tissue of differing impedances such that the power remains the same. This normalization tunes the output power to match to the average tissue impedance of the target tissue.

In some embodiments, the impedance discriminator 336 is employed to provide two separate, but related functions to the PWM output 318 of the RF power generator 334, including low-pass filtering and impedance load discrimination. The low pass filter minimizes the resultant higher order odd harmonics associated with the square-wave in the output to produce the sine wave output to the instrument 12 from the inputted square wave generated by the PWM generator circuit 336.

Figure 6:
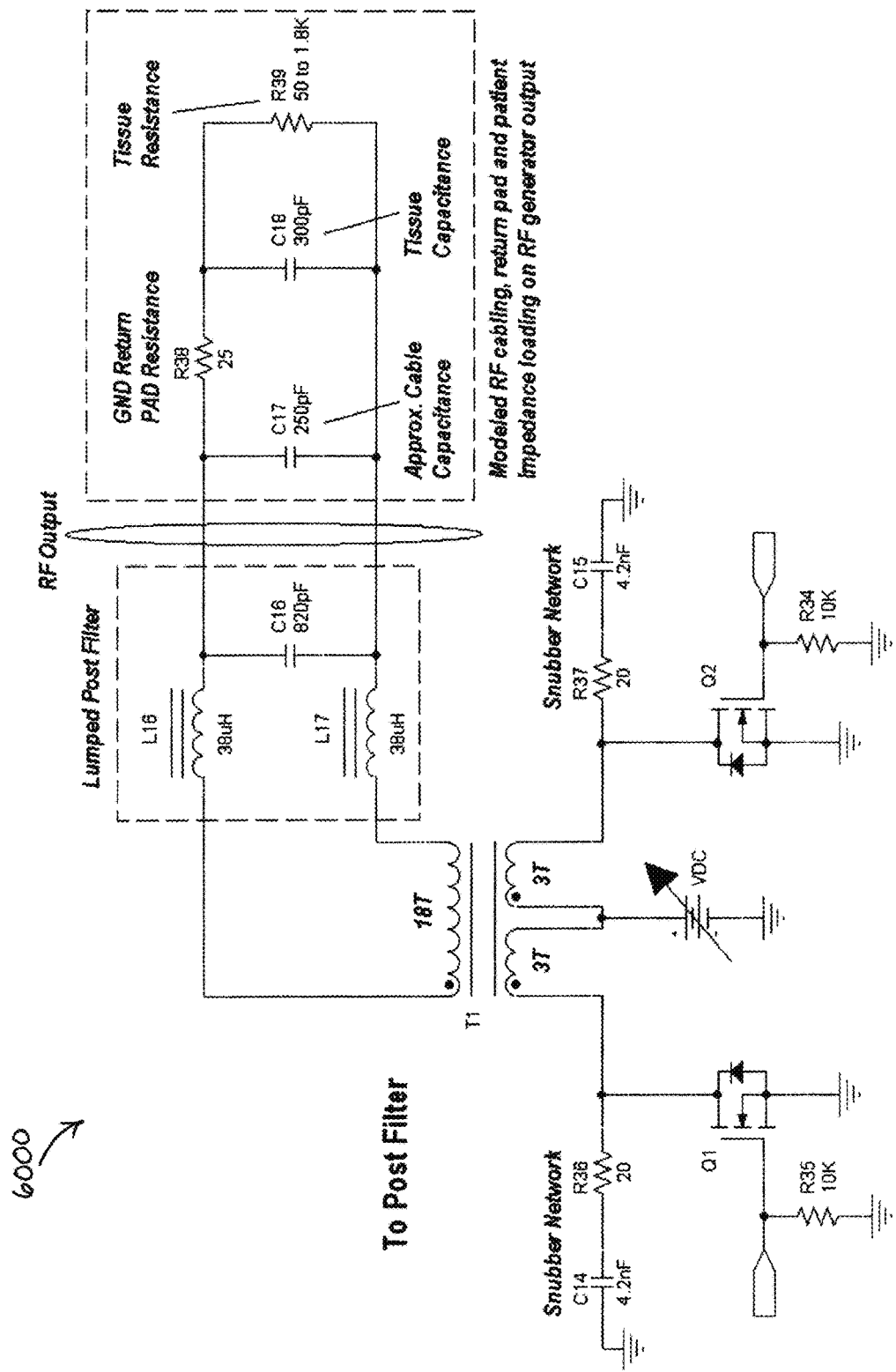
FIG. 6 illustrates an example impedance discriminator circuit according to an illustrative embodiment.

FIG. 6 illustrates an example impedance discriminator circuit 6000 according to an illustrative embodiment. This stage provides two separate, but related functions to the 340 KHz squarewave coming from the secondary of the RF chopper transformer shown in FIG. 6, namely: low pass filtering and impedance load discrimination. The low pass filter simply minimizes the resultant higher order odd harmonics associated with the RF 340 KHz squarewave, i.e., 3f, 5f, 7f, etc. in the output.

The patient load discrimination function is a result of what kind of low pass filter is chosen. In this case, a Butterworth low pass was chosen with an under damped Bode response at 1800 ohms at R39. This modeled patient resistance has been estimated from a number of laboratory experiments to be from 50 to 1800 Ohms. Phase shift at higher patient resistances models show the tissue capacitance to be around 300 pico farads (pF) ±20% as shown in FIG. 6 as C18.

If we derive a simple Laplace transfer function model for the output circuit shown in FIG. 6, we can assume the source to be a voltage source and the output voltage across the patient modeled resistance, R39, we have the following transfer function:

$$H := 0.4 \cdot 10^{24} R39(0.300274 \cdot 10^{16} s\ R39 + 0.4 \cdot 10^{24} R39 + 0.1000200000\ 1026 + 0.5480001605\ 10^{11}\ s2R39 + 321.\ s3\ R39 + 0.1070000000\ 1013s2 + 0.4000005350\ 1020s)$$ (Equation 2)

From Equation 2 a third order low pass function is observed. A 3D plot shows the dependence of the voltage transfer of the post filter upon the patient resistance and frequency as shown in FIG. 7.

Also shown in FIG. 6 is an RF output filter including inductors L16, L17 and capacitor C16. It will be appreciated that in some embodiments, capacitor C16 can comprise one or more polypropylene capacitors to achieve a relatively high power rating.

Figure 7:
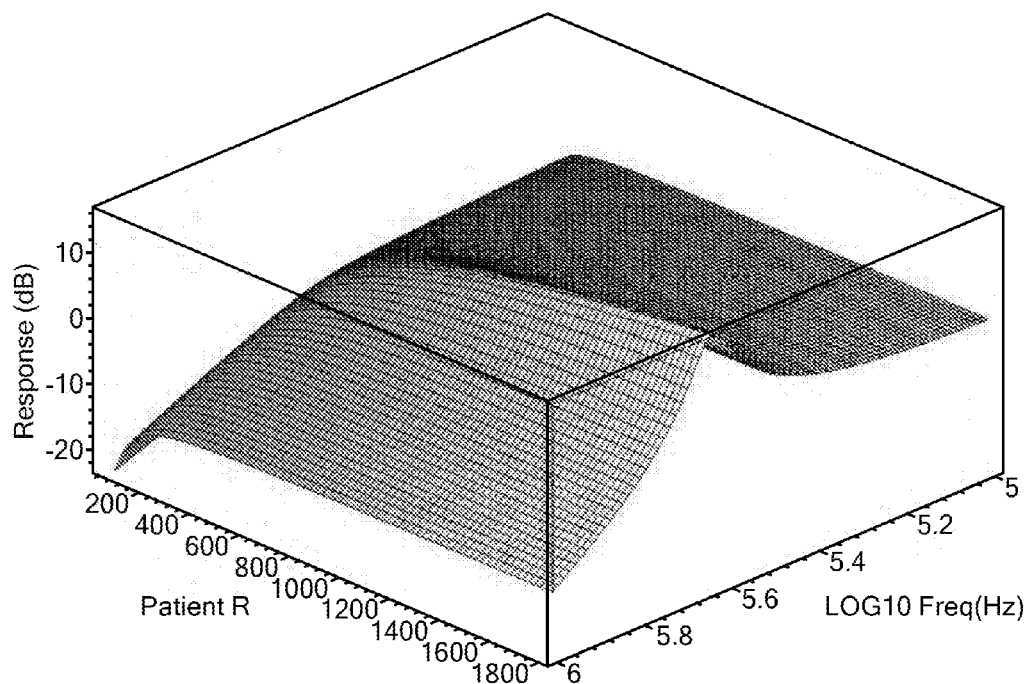
FIG. 7 is a 3D plot that illustrates the dependence of the voltage transfer of the post filter upon the patient resistance and frequency.

FIG. 7 shows that at the higher patient resistance, the peaking function is dramatic relative to the patient resistance at around 500 ohms and less. It is this dynamic that is desired to minimize the effect when ablating through in high impedance tissue (e.g., fatty tissue) and suddenly encountering a low impedance tissue (e.g., skeletal or connective tissue). As an example, without the discriminator circuit, if the RF generator was outputting 100 Watts while ablating through a high impedance tissue (e.g., having a value about 1800 ohms) and then encounters a lesser impedance tissue (e.g., having a value about 50 ohms), the power is subsequently increased from 100 W to 3600 W. This tremendous increase of power density poses a risk of damage for the probe. This along with a tremendous increase of power density at the low resistance contact point (usually some relatively small area on the loop wire) on the probe almost insures destruction of the wire/probe assembly.

Figure 8:
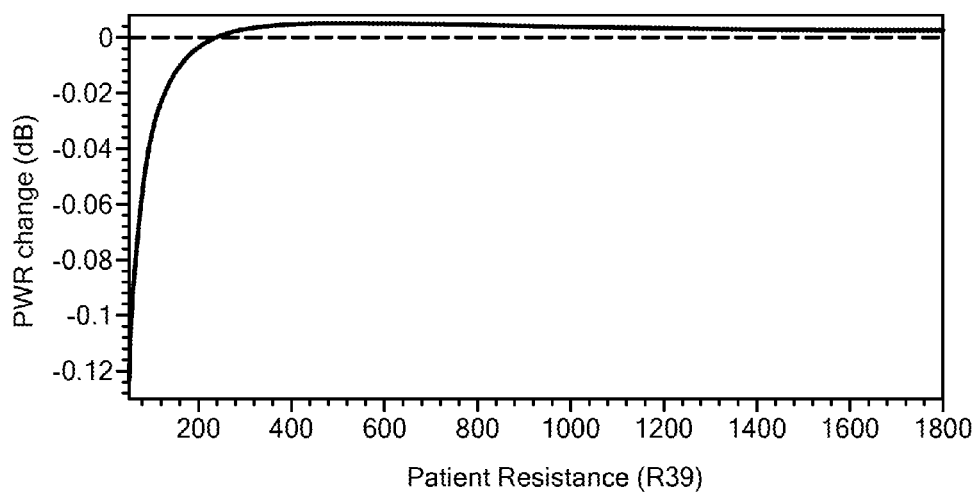
FIG. 8 is a plot of the change in power over a range of tissue impedance.

Using the impedance discriminator, the power delivered to the patient load between the intended impedance range (e.g., between about 50 and about 1800 ohms) remains about the same across the range. FIG. 8 illustrates a plot of the change in power over a range of tissue impedance. As shown, the change in delivered power remains consistent over the intended impedance range.

Moreover, the post filter network topology can be designed to reduce the delivered RF patient power to less than that at the higher patient impedances. The power drop factor can be experimentally determined. It is noted that too much power reduction, e.g., due to aggressive impedance discrimination, can result in a loss of low-impedance tissue plasma ignition, which may result in the arc not being as effective in ablating through the tissue.

RF Average Voltage, Current, and Power Monitoring and Phase Angle Measurement As discussed above, a phase-angle measurement of the actual power is employed by the present controller, in some embodiments, to adjust the output power to enable a uniform real-power density for the cutting arc. The phase-angle measurement enables the calculation of a differential phase angle, shown as "angle Z" in Equation 3.

$$P = \frac{V_{RMS}^2}{|Z|} \times \cos(\text{angle } Z)$$ (Equation 3)

The differential phase angle is a measurement of the relative phase, or time delay, between two waveforms, namely the sinusoidal waveform of the delivered current and the sinusoidal waveform of the delivered voltage. This phase angle reduces the net transfer of energy, in one direction.

When ablating through tissue, it has been observed that the power factor (namely, the ratio of real power that is used to do work and the apparent power that is stored) of the delivered power can vary greatly due to varying impedances of the various tissues, resulting in erroneous power readouts and controls. The differential phase angle (angle Z) provides the relative phase offset between the current and voltage waveforms which can be employed to maintain the average real-power delivered to the cutting arc to the desired power levels. The differential phase angle (angle Z) can be expressed as θ, as shown in Equation 4, and is determined, in some embodiments, by a phase-angle measurement derived from a root-mean square current measurement $I_{OUT}^{RMS}$ and a root-mean square voltage measurement $V_{OUT}^{RMS}$.

$$\theta = \cos^{-1}\left[\frac{\langle P_{OUT}(t)\rangle}{V_{OUT}^{RMS} I_{OUT}^{RMS}}\right] \quad \text{(Equation 4)}$$

Referring again to FIG. 1, in some embodiments, the root-mean square current measurement (326) and root-mean square voltage measurement (328) are measured via transformers 320 and 322 connected at the output ports 340 to the instrument and converted to root mean square values. A power feedback measurement 344 corresponding to the average power delivered ($P_{sense}$) is measured using outputs 326', 328' of the voltage transformer ($V_{sense}$) and the current transformer ($I_{sense}$). The measurements 326' and 328' are combined, via a multiplier 324, as v(t) x i(t), and are filtered via a low pass filter 332, to produce the average power output 330. In some embodiments, a single pole 2.5 kHz low-pass filter is employed. The average power output 330 is captured, in some embodiment, via an analog-to-digital converter (ADC) 342. The PID controller 300 compares the captured average power measured ($P_{sense}$) 344 to the desired power profile 302 and sets the output level of the RF generator accordingly. Stated differently, the controller 300 selects a control setting (e.g., power curve) 302 stored in memory 303 for the identified, attached wand 12 from the stored plurality of control settings, each associated with a different type of wand, and compares the measured output power 344 to the control setting 302 to adjust the delivered RF energy accordingly.

As shown in FIG. 1, the output 310 of the PID controller 300 is received by a square-root function linearizer 308. In this control topology, non-linearity can result because the output 310 of the PID controller is referenced to power while the control signal of the RF generator (DC-DC-CMD) is set to voltage. This non-linearity is due to the output power being proportional to the square of the output voltage while being inversely proportional to the load impedance. The linearizer 308 prevents a non-linear outputs from resulting, as shown in Equation 3.

The output as a digital signal, shown as 312, is converted to an analog command ($V_{PROG}$) 316, via a digital-to-analog converter (DAC) 314, and is converted to PWM signals, e.g., in a RF chopper circuit, via a PWM generator 334. The output 318 of the PWM generator 334 is filtered by a post-filter/impedance matching network 336 to provide a high-frequency current and voltage output 340, as a sine wave, to the electrosurgical device 12.

When ablating fatty tissue, it is observed that the power factor of the delivered power can drop from near unity in highly conductive media to 0.30 with the resulting erroneous readout resulting from a simple $V_{OUT}^{RMS} \times I_{OUT}^{RMS}$ product. These delivered power readings will always read much higher than the actual delivered RF power (as much as 2:1).

It is imperative to know the phase angle to determine the actual RF power being delivered. In some embodiments, use of the phase angle and actual RF power information can enable controls that maintain uniform real power density throughout the exposed length of the wand cutting cable.

Figure 9:
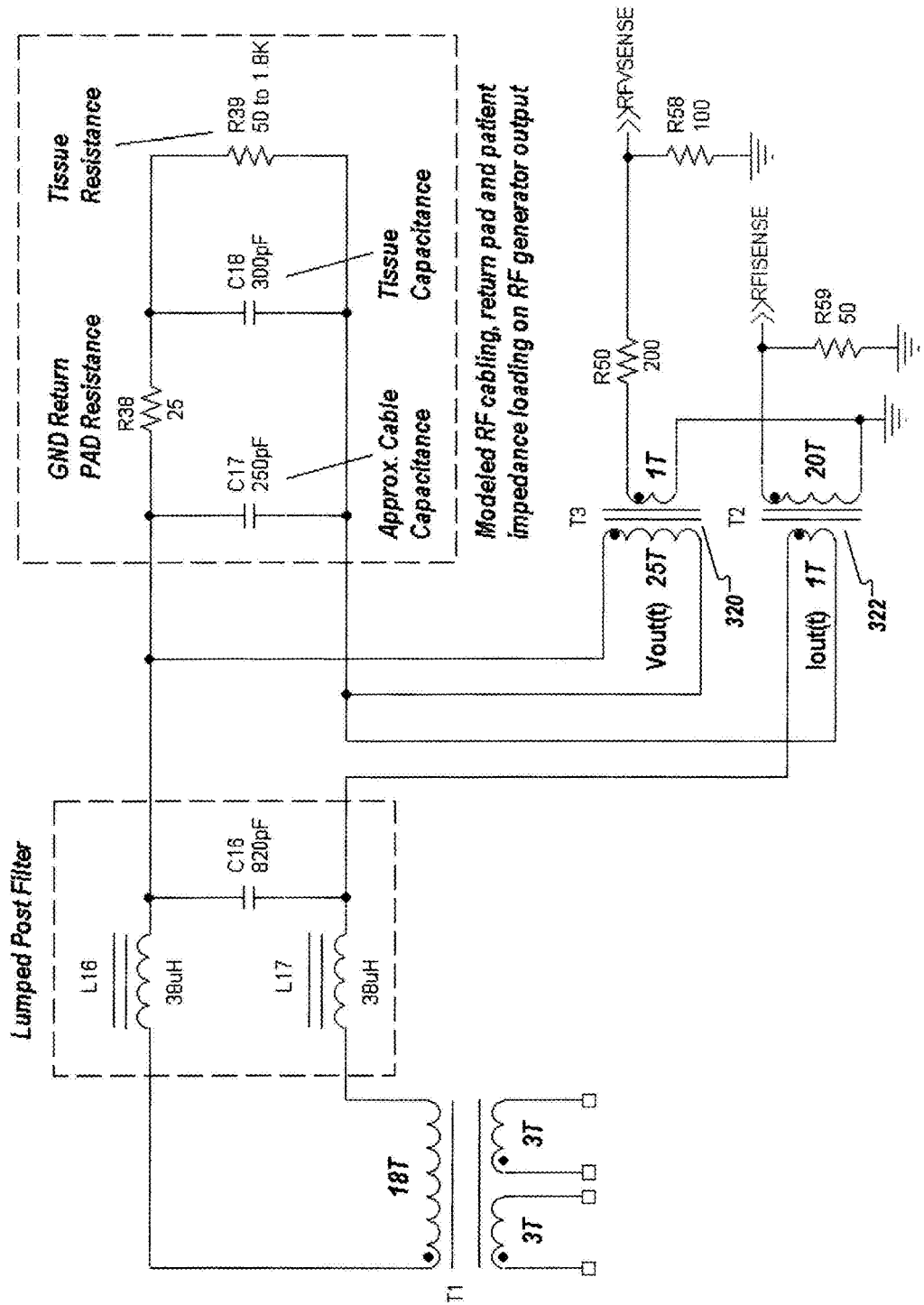
FIG. 9 illustrates a phase-angle measurement circuit according to an illustrative embodiment.

FIG. 9 illustrates a phase-angle measurement circuit according to an illustrative embodiment. Specifically, FIG. 9 shows the phase-angle measurement circuit implemented as a RF output voltage and current sense transformers (320, 322). The transformers are configured to acquire the time-based real-time RF voltage and current waveforms at the patient load port. The magnetics used are observed to yield excellent signal integrity with regard to both magnitude and phase between the voltage and current waveforms.

From FIG. 9, the RF voltage sense and current sense equations are provided in Equations 5 and 6.

$$RFVSENSE(t) = \frac{1}{75}V_{OUT}(t) \quad \text{(Equation 5)}$$

$$RFISENSE(t) = \frac{5}{2}I_{OUT}(t) \quad \text{(Equation 6)}$$

The expressions for $V_{SENSE}^{RF}(t)$ and $I_{SENSE}^{RF}(t)$ are provided, in some embodiments, into an analog multiplier IC 324 (FIG. 1) with an offset adjustment to determine $P_{SENSE}$. The output of the multiplier (shown as Multiplier(t)) is provided in Equation 7.

$$\begin{aligned}\text{Multiplier}(t) &= \frac{RFVSENSE(t) \times RFISENSE(t)}{10} + V_{OFFSET} \\ &= \frac{V_{OUT}(t) \times I_{OUT}(t)}{300} + V_{OFFSET}\end{aligned} \quad \text{(Equation 7)}$$

The result of multiplier from Equation 7 is subsequently filtered, in some embodiments, via a low-pass filter (e.g., 322) to determine an average value of the power output, $P_{SENSE}$. As shown in Equation 8, the output is multiplied by a gain of five (5) to create the final time-averaged power expression, Final_Multiplier(t).

$$\text{Final\_Multiplier}(t) = \frac{5}{T}\int_0^T \left(\frac{V_{OUT}(t) \times I_{OUT}(t)}{300} + V_{OFFSET}\right)dt \quad \text{(Equation 8)}$$

$V_{OFFSET}$, in Equation 8, represents a DC error value, which may be nulled through calibration. To this end, the term for $V_{OFFSET}$ may be adjusted to nearly zero allowing Equation 8 to be simplified, as shown in Equation 9.

$$\begin{aligned}\text{Final\_Multiplier}(t) &= \frac{1}{60T}\int_0^T (V_{OUT}(t) \times I_{OUT}(t))dt \\ &= \frac{1}{60}\langle P_{OUT}(t)\rangle\end{aligned} \quad \text{(Equation 9)}$$

Hence, the final result is the averaged real power (in Watts) scaled down by 1/60. This computation is passed to the digital controller 300 along with the RMS values for the current and voltage. In some embodiments, the RMS values for the current and voltage (RVSENSE(t) and RFISENSE(t)) are determined during a Sigma-Delta RMS Converter ICs, e.g., model no. LTC1968CMS8. The differential phase angle can be computed with these inputs within the digital controller using the expression shown in Equation 10.

$$\langle P_{OUT}(t)\rangle = V_{OUT}^{RMS} I_{OUT}^{RMS} \cos(\theta) \quad \text{(Equation 10)}$$

Therefore, the differential phase angle $\theta$ can be computed as shown in Equation 11.

$$\theta = \cos^{-1}\left[\frac{\langle P_{OUT}(t) \rangle}{V_{OUT}^{RMS} I_{OUT}^{RMS}}\right] \quad \text{(Equation 11)}$$

In certain embodiments, it is imperative to know the phase angle because when the user is ablating fatty tissue, the power factor can drop from near unity in highly conductive media to 0.30 with the resulting erroneous patient power readout resulting from a simple product. These delivered power readings will always read much higher than the actual delivered RF power (as much as 2:1).

FIGS. 10 and 11 illustrate example converter circuits 350 and 351 to convert the $V_{out}(t)$ and $I_{out}(t)$ to RMS values, $V_{OUT}^{RMS}(t)$ and $I_{OUT}^{RMS}(t)$, respectively. The circuits 350 and 351 employs a Sigma-Delta RMS Converter ICs, e.g., Model No. LTC1968CMS8 (by Linear Technology).

Figure 12:
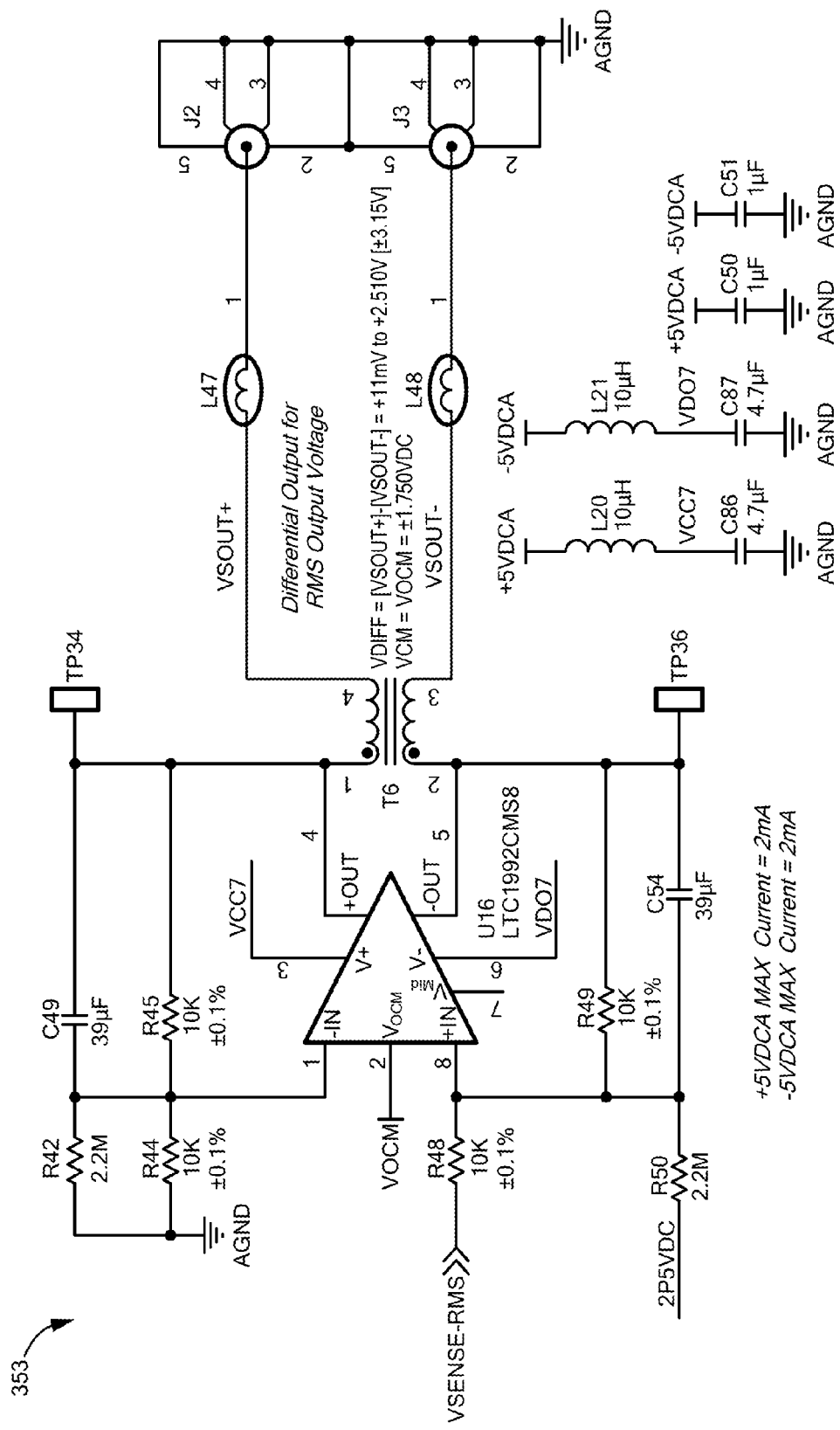
FIGS. 12, 13, and 14 illustrate example post processing circuits to provide differential output signals for the average voltage, current, and power measurements.
Figure 13:
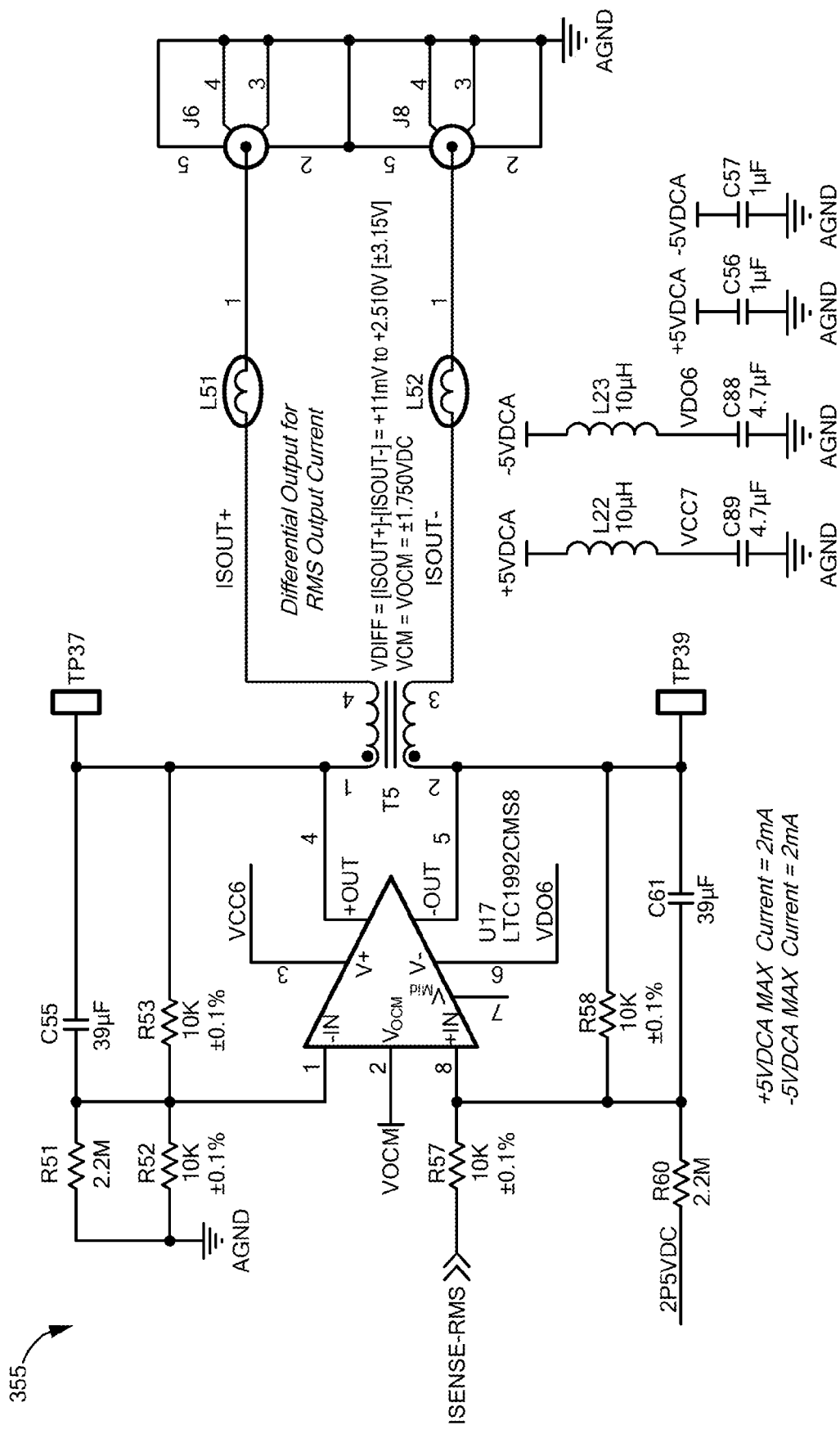
Figure 14:
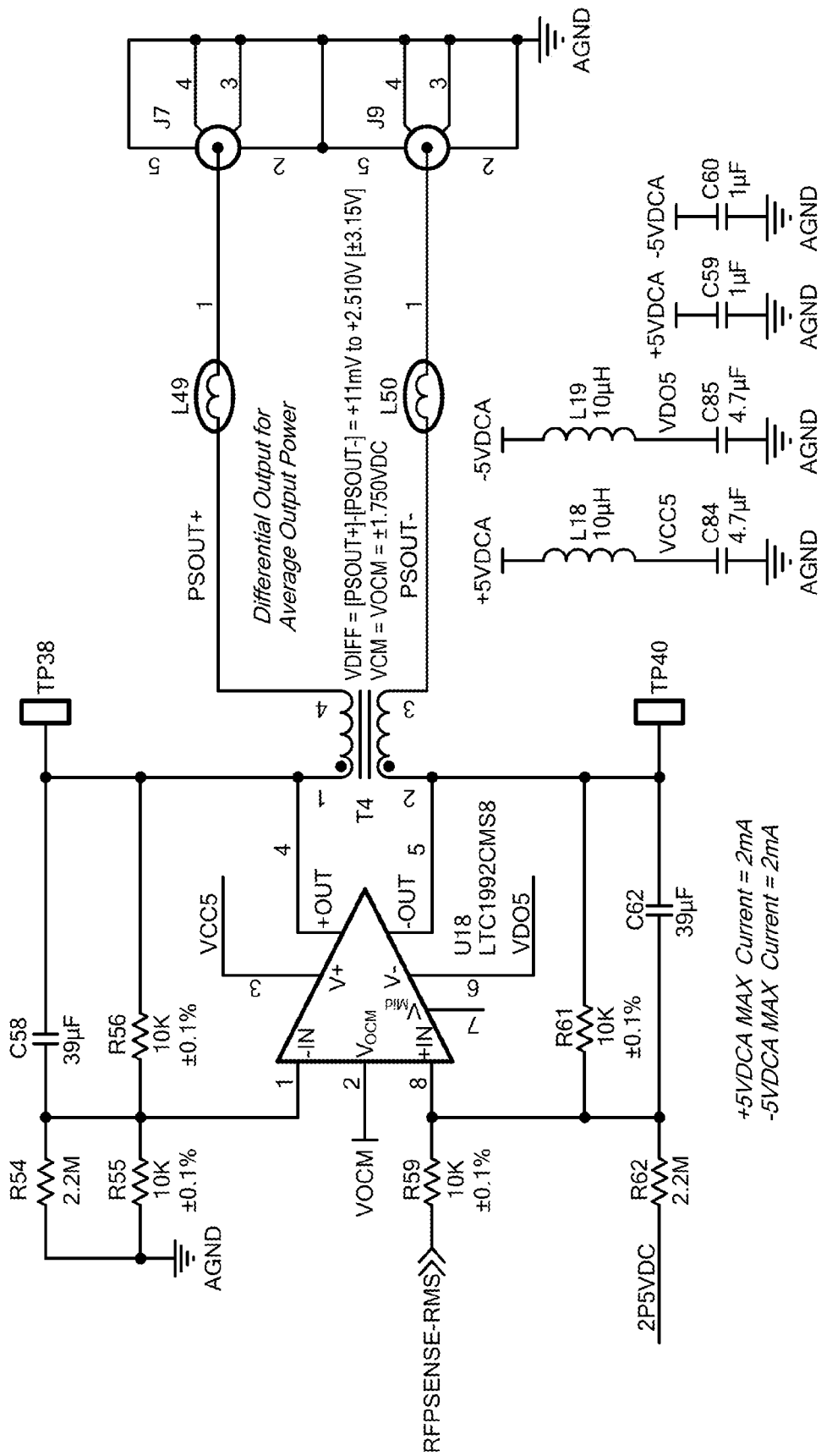

FIGS. 12 and 13 illustrate example post processing circuits 353, 355 to provide differential outputs for the $V_{OUT}^{RMS}(t)$ and $I_{OUT}^{RMS}(t)$ outputs of circuits 353 and 355. The outputs from circuits 353 and 355 are converted via a A/D converter and inputted into a FPGA-based controller. The differential outputs formats the output signals of circuits 353 and 355 to the input range of the A/D converters. FIG. 14 illustrates an example differential output for average power output, $P_{OUT}(t)$. In some embodiments, a 16-bit ADC is used to sample the signals. Details of the signal characteristics for the voltage and current measurements are provided in Table 1.

TABLE 1

| Signal | I/O | Levels | Description |
| --- | --- | --- | --- |
| HV_V | Input | 0-12 V | Rectified AC output of the RF generator, stepped down by 40:1. 4.4 V @ 1000 Vp-p. Sending impedance 1.5K Ohms in parallel w/100 pF. |
| HV_I+ | Input | Max current = 10 mA rms | HV_I+ and HV_I− connected to a current transformer with a step down of 200:1 |
| HV_I− | Input | Max current = 10 mA rms | |
| VOUT | Output | TBD | A voltage proportional to RMS RF voltage, scaled to match the input range of the ADC. Required bandwidth 0-100 Hz |
| IOUT | Output | TBD | A voltage proportional to RMS RF current, scaled to match the input range of the ADC. Required bandwidth 0-100 Hz |

The disclosed technology may further be employed in other example electrosurgical generators, for example, those disclosed in U.S. Pat. Nos. 6,740,079 and 6,923,804, the contents of each of these applications are incorporated by reference herein in their entireties.

Figure 15:
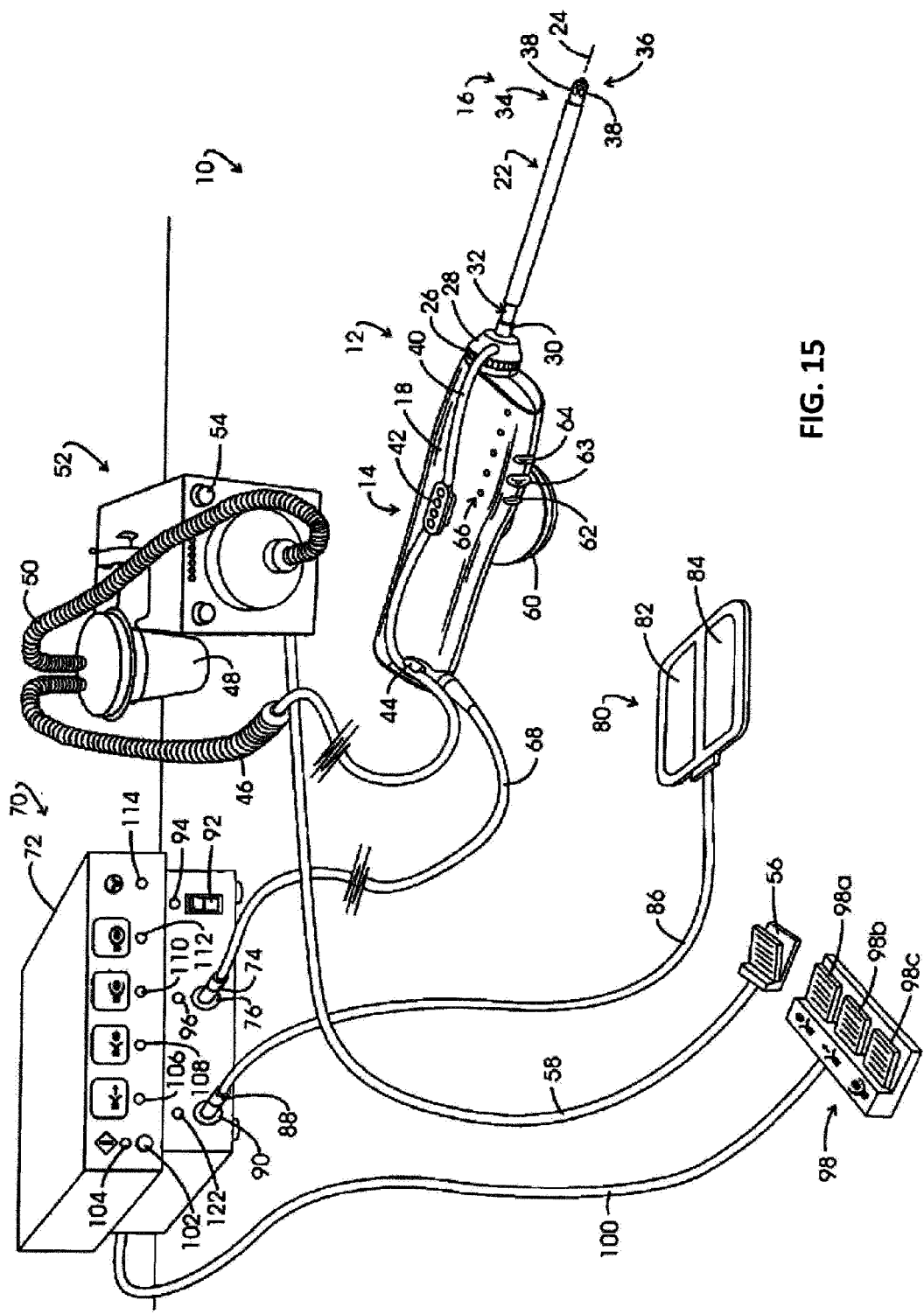
FIG. 15 is a perspective view of an electrosurgical system according to an illustrative embodiment.
Figure 16:
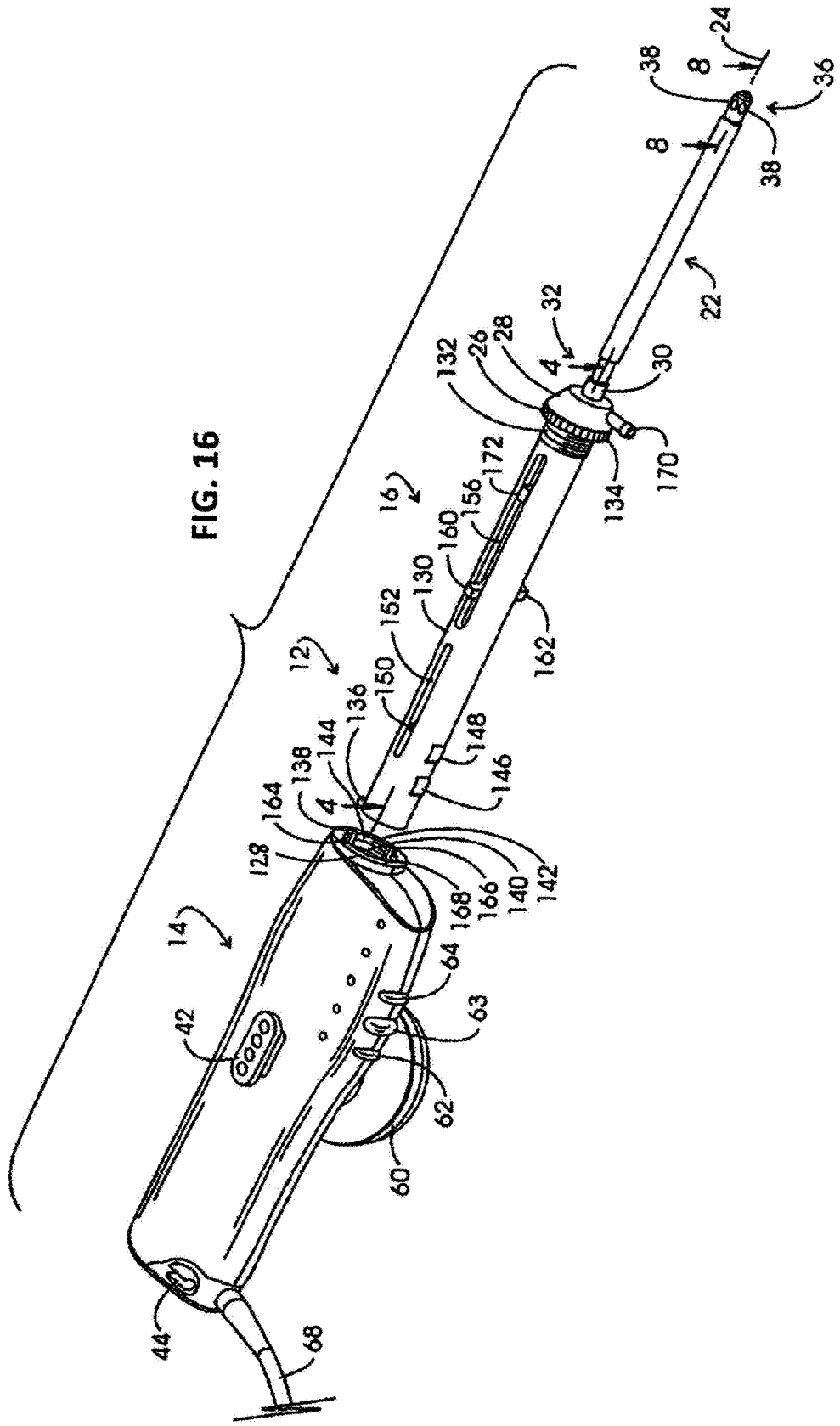
FIG. 16 is an exploded view of an electrosurgical instrument shown in FIG. 15.
Figure 19:
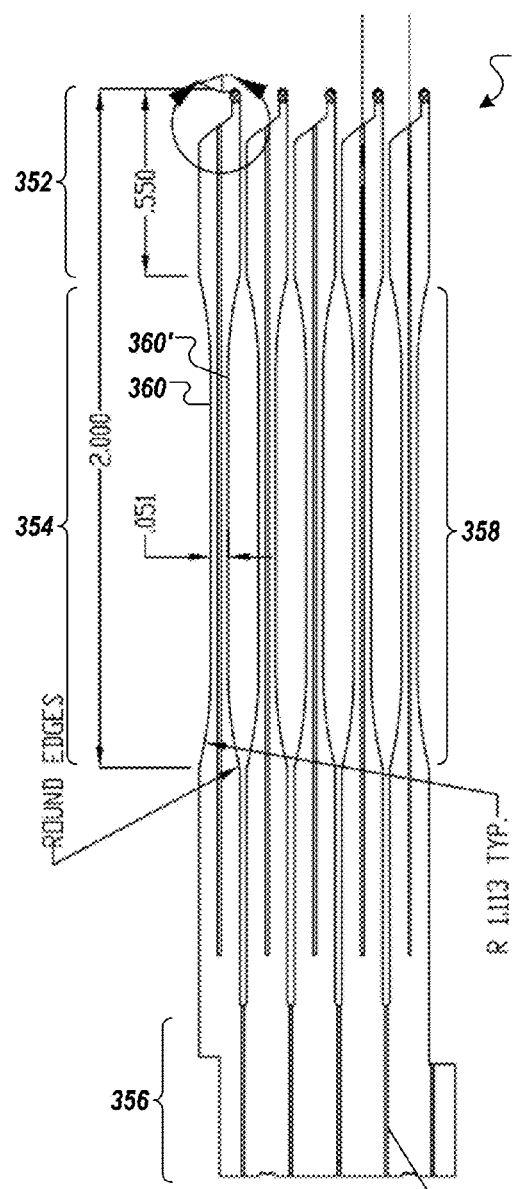
FIG. 19 is a top view schematic of a capture component assembly with capture components having varying stiffness according to the illustrative embodiment.

FIG. 15 illustrates an example electrosurgical system 10 with a handheld capture instrument 12 that can employ the struts 20 exemplified herein (see FIG. 19). The capture instrument 12 (also referred to as a "wand"), in some embodiments, includes a reusable handle component 14 that attachably mates with a disposable single-use delivery component 16 (also referred to as a "probe"), as shown in FIG. 16. In some embodiments, the struts 20 extend along the length of the delivery component 16 to be actuated from the forward tip of the delivery component 16, as shown in FIGS. 17 and 18, which depict struts 20A of uniform widths. The struts 20 exemplified herein, shown in FIG. 19, include a full width initial section 352 that forms the stiff forward section of the struts and precedes a narrower middle section 354.

Figure 21:
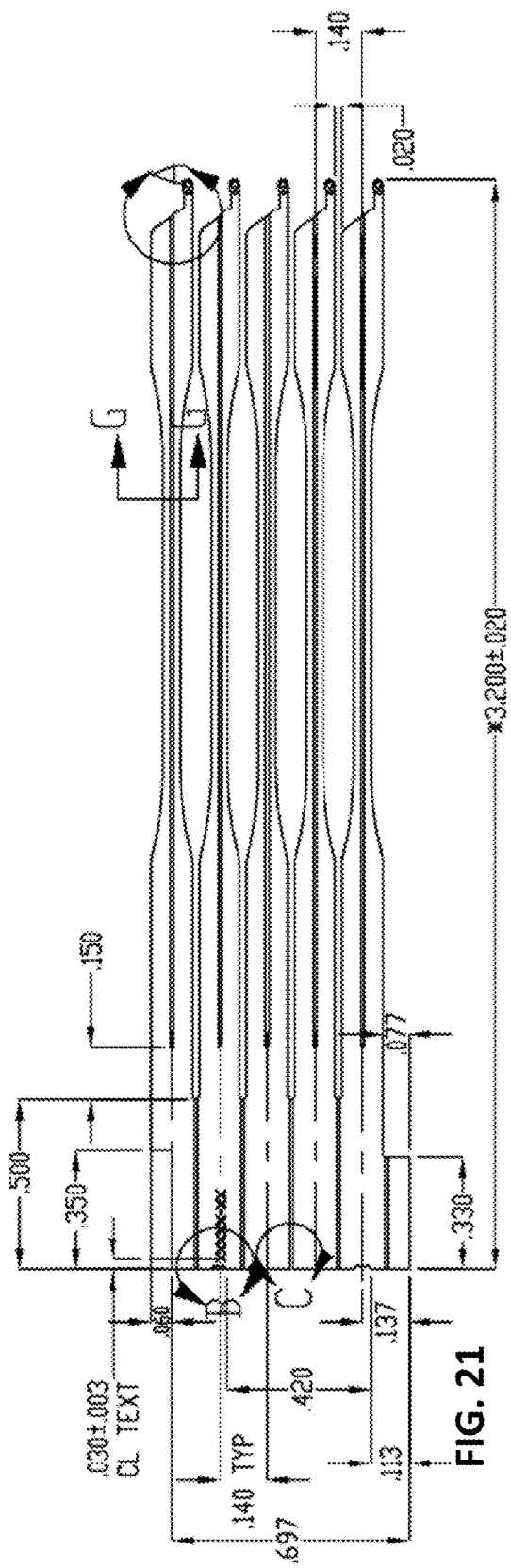
FIG. 21 is another top view schematic of the capture component assembly of FIG. 19 according to the illustrative embodiment.
Figure 22:
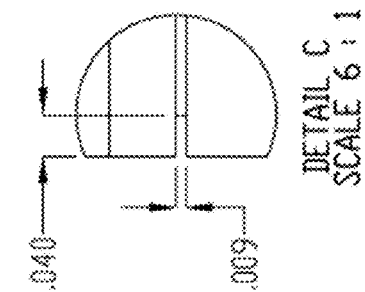
FIG. 22 is a detailed side view of a cross-section of the flexible mid-region of a capture component of the capture component assembly of FIG. 21.
Figure 23:
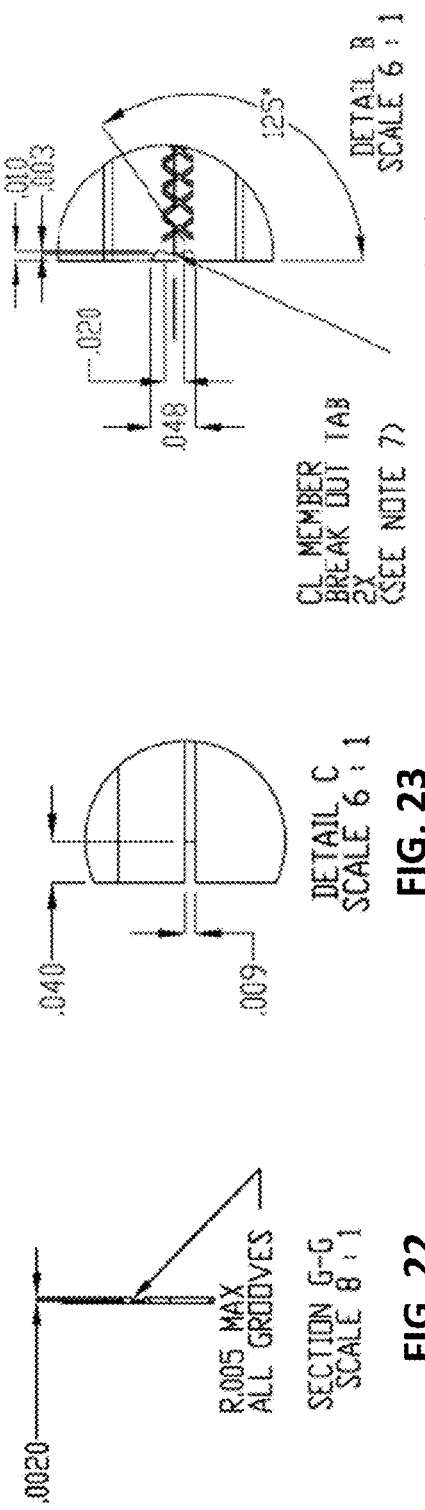
FIG. 23 is a view of a base region of the capture component assembly of FIG. 21.
Figure 24:
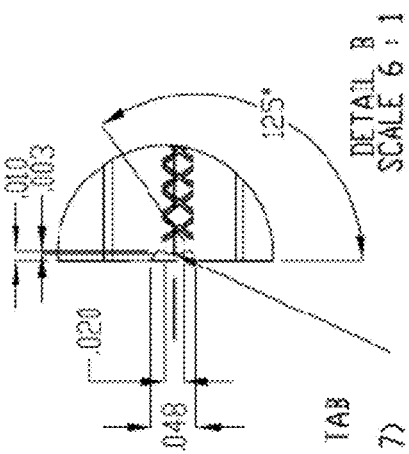
FIG. 24 is a view of a break-out tab of the capture component assembly of FIG. 21.

As shown in FIG. 19, the forward section 352 and middle section 354 are connected, in some embodiments, via a base 356 to form a single contiguous structure. In some embodiments, the forward region 352 transitions to a narrower middle region 354 to form a concave section 360 and 360'. The concave sections 360, 360' are located on each side of the strut 20 such that the struts somewhat resembles an elongated hourglass. Example dimensions for the struts 20 that can be assembled into the delivery component 16 to provide a maximum diametric capture width of 30 mm are provided in FIGS. 19 and 21.

Figure 20:
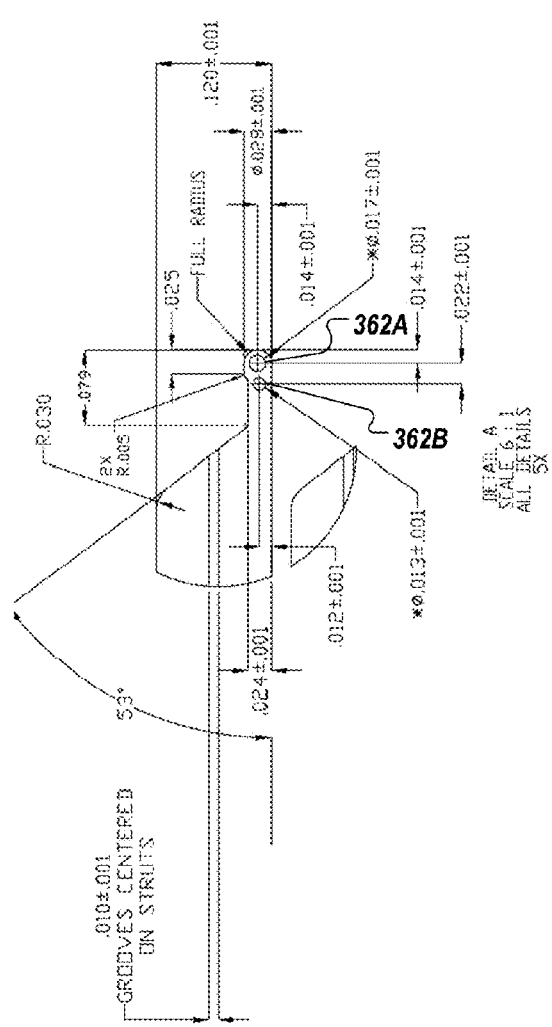
FIG. 20 is a detailed view of an eyelet structure of a capture component of the capture component assembly of FIG. 19.

Each strut 20 includes, in some embodiments, one or more eyelets, shown as 362A, 362B in FIG. 20, at its forward tip. In some embodiments, one or more electrosurgical filaments (also referred to as "cutting cables 250") are employed to extend through a forward eyelet 362A on each strut and then tied off at a second eyelet 362B of a nearby strut. Consequently, the cutting cables 250 and struts 20 form a cutting arc face, as for example, shown in FIGS. 26 and 27, when the cutting cables 250 are energized. In some embodiments, the first eyelets 362A allow for the cutting cable 250 to pass therethrough (see FIGS. 26 and 27) to allow for the expansion and contraction of the cutting face during the deployment process. In some embodiments, the first eyelets 362A and second eyelets are of different sizes. In other embodiments, the eyelets 362A and 362B are of the same size.

In some embodiments, the cutting cable 250 consists of five (5) small diameter wire cables for cutting tissue with a mono-polar electro-surgical cutting current. The cutting cable 250, in some embodiments, is configured to purse down to close the distal end of the cutting/capture element to make a circumscribing incision and capture of the target tissue.

Figure 26:
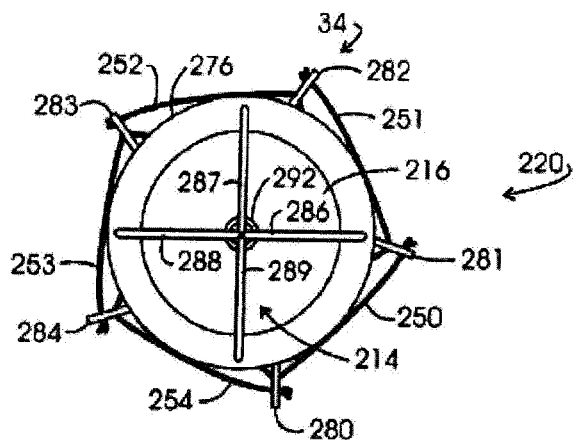
FIG. 26 is a front view of an example electrosurgical instrument showing the capture components in a retracted orientation.
Figure 27:
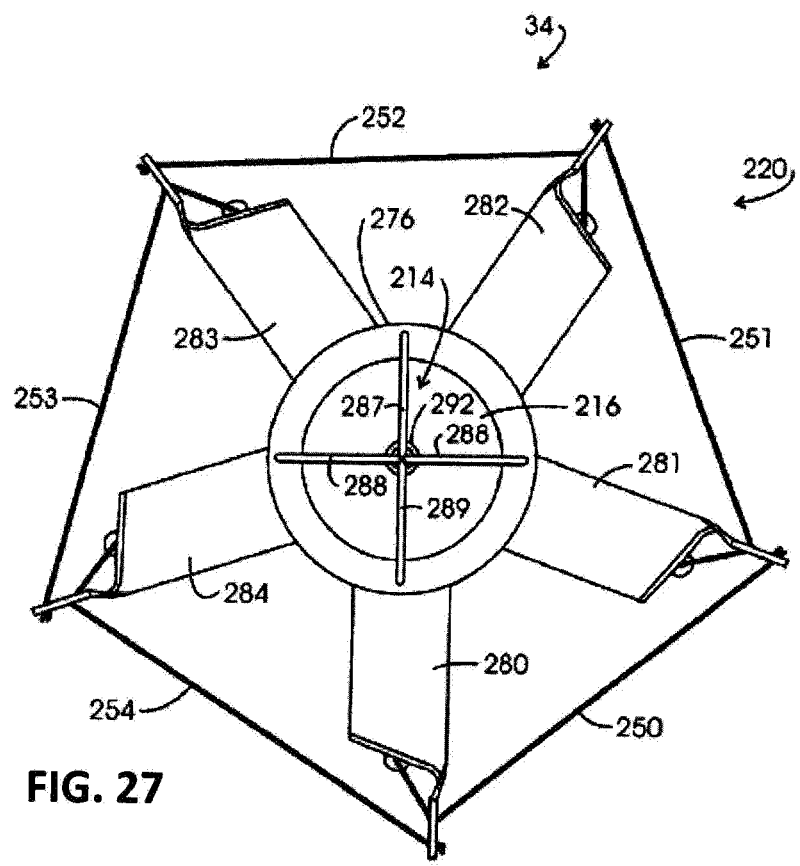
FIG. 27 is a front view of an example electrosurgical instrument showing the capture components at a stage in its deployment.

Looking to FIG. 26, the initial orientation of the cutting cables shown as 250-254 is revealed in which the cables 250-254 are drawn across the surface 276 of the forward region 34. As shown, the cables 250-254 are drawn through second eyelets 362B on each respective strut 20, shown as struts 280-284, and tied off at first eyelets 362A on a nearby strut. In this regard, cable 250 extends through the second eyelet in strut 280 and is tied off at the first eyelet of the strut 281. Similarly, cable 251 extends through the second eyelet of strut 281 and is tied off at the first eyelet of strut 282; cable 252 extends through the second eyelet of strut 282 and is tied off at the first eyelet of strut 283; cable 253 extends through the second eyelet of strut 283 and is tied off at the first eyelet of strut 284; and cable 254 extends through the second eyelet of strut 284 and is tied off at the first eyelet of strut 280.

Figure 28A:
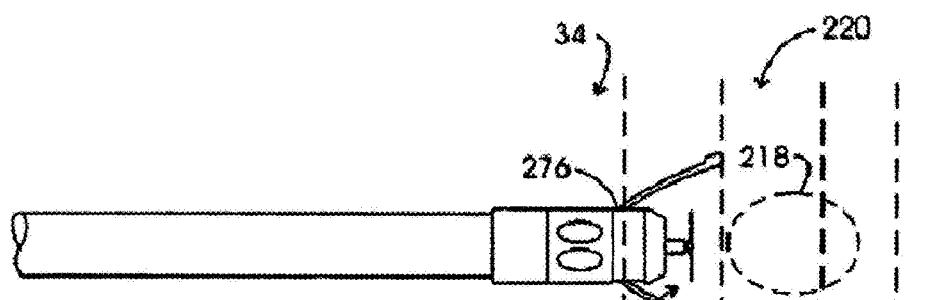
FIGS. 28A, 28B, and 28C illustrate a sequence of a capture procedure.
Figure 28B:
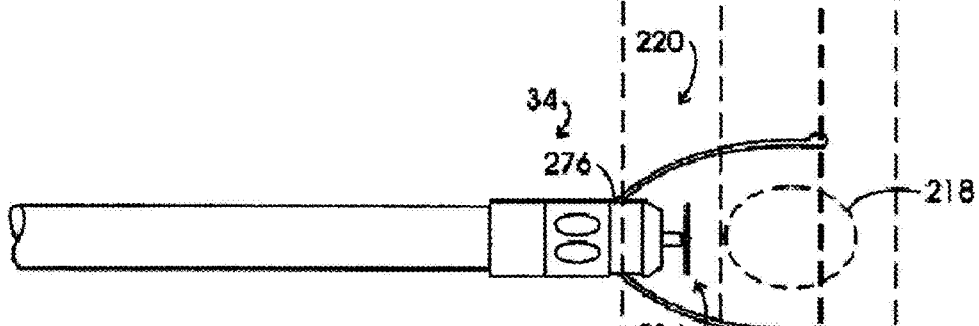
Figure 28C:
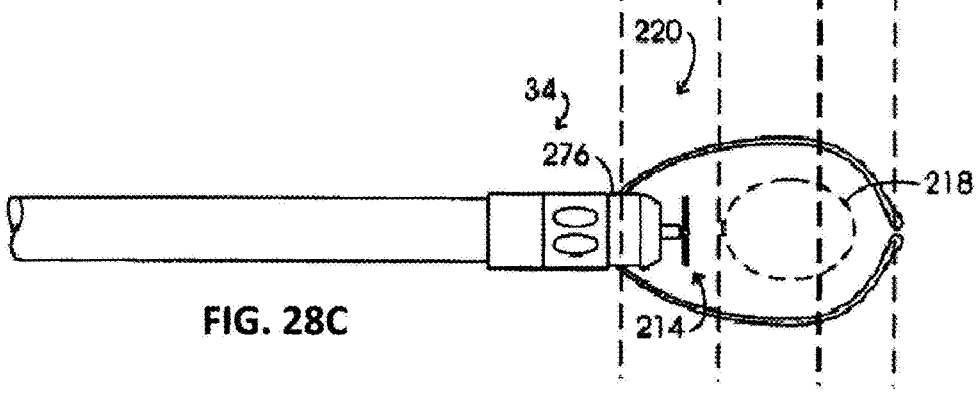

An example deployment sequent of the struts 20 and cutting cable 250 is shown in FIGS. 28A, 28B, and 28C. As shown in FIG. 28A, following initiation of the deployment process, the struts 20 (i.e., capture components) are forwardly extended at a trajectory (i.e., a first extension) having an axial component and a radial expansion component, e.g., at a trajectory of about 45 degrees. In some embodiments, the struts 20 extend from the probe (i.e., elongated shaft) along a first region corresponding to the stiffer uniform-width forward region 352 of the struts 20. The stiffer region of section 352 allows the struts 20 to consistently extend at the intended trajectory in a uniform manner.

Subsequently, the one or more capture components and one or more cutting cables inwardly extend by contraction (e.g., stoppage) of the cutting cables relative to the capture component at a contraction region, as shown in FIGS. 28B and 28C, along a second stiffness region corresponding to the concave region 354 of the struts 20. The capture components and cutting electrodes may still extend in a direction having a radial expansion component, as shown in FIG. 28B. Following a position along the elliptical path defining the maximum diametric capture size of the apparatus, as shown in FIG. 28C, the capture components and cutting electrodes are traveling forwardly having an axial component and a radial contraction component (i.e., a second extension). The second stiffness region provides a reduction in stiffness (relative to the first stiffness region) that is observed to yield a wand performance with the maximum possible basket diameter and the most uniform shape observed to date.

The first extension, having the first axial component and the radial expansion component, may result from the plurality of capture components and one or more electrosurgical filaments being extendable at the same travel rate. The second extension, having the second axial component and the radial contraction component, may result from i) the plurality of capture components being extendable at a first travel rate and the one or more electrosurgical filaments being extendable at a second travel rate, the first travel rate being greater than the second travel rate. In some embodiments, the narrow section of the strut 20 has a similar or same stiffness to the standard wide struts used in proven working (e.g., of 10-mm to 20-mm devices) design having been used in nearly 50,000 biopsies to date.

In some embodiments, the struts 20 are formed as a single structure with a folding line 362 (FIG. 19) formed among them. The folding lines allow the struts 20 to form a pre-assembly, as for example shown in FIG. 25A, that can be integrated into the probe component 16.

To power the electrosurgical device, the device is electrically coupled, in some embodiments, to a high-frequency power generator that may be the same as or similar to the RF generator described herein.

Figure 37:
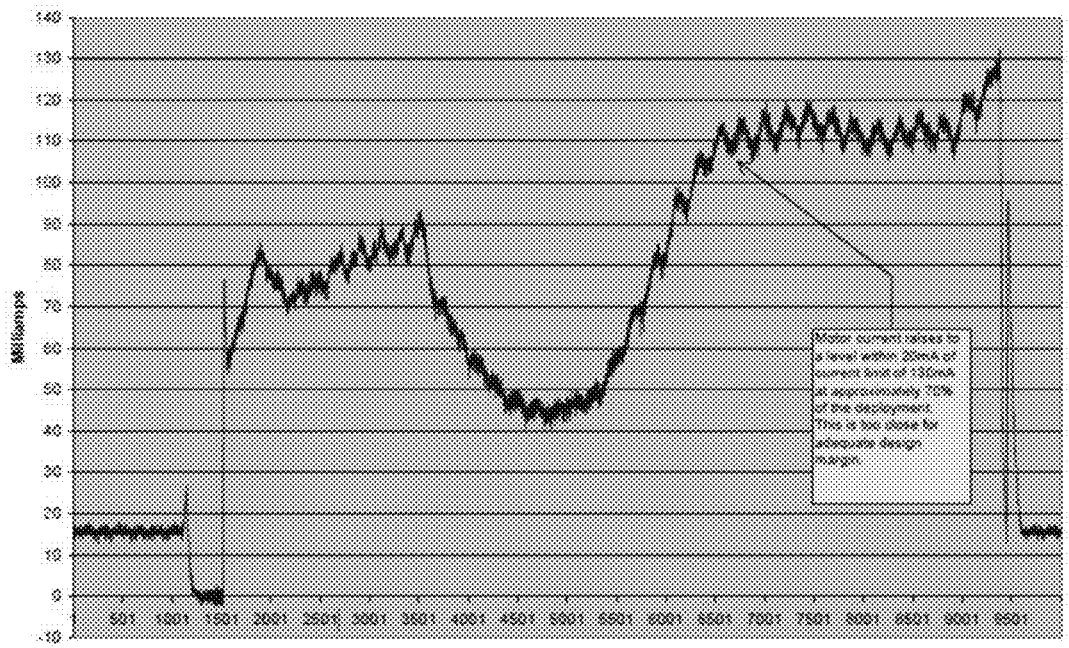
FIGS. 37 and 38 are diagrams illustrating motor current draw of an electrosurgical device.
Figure 38:
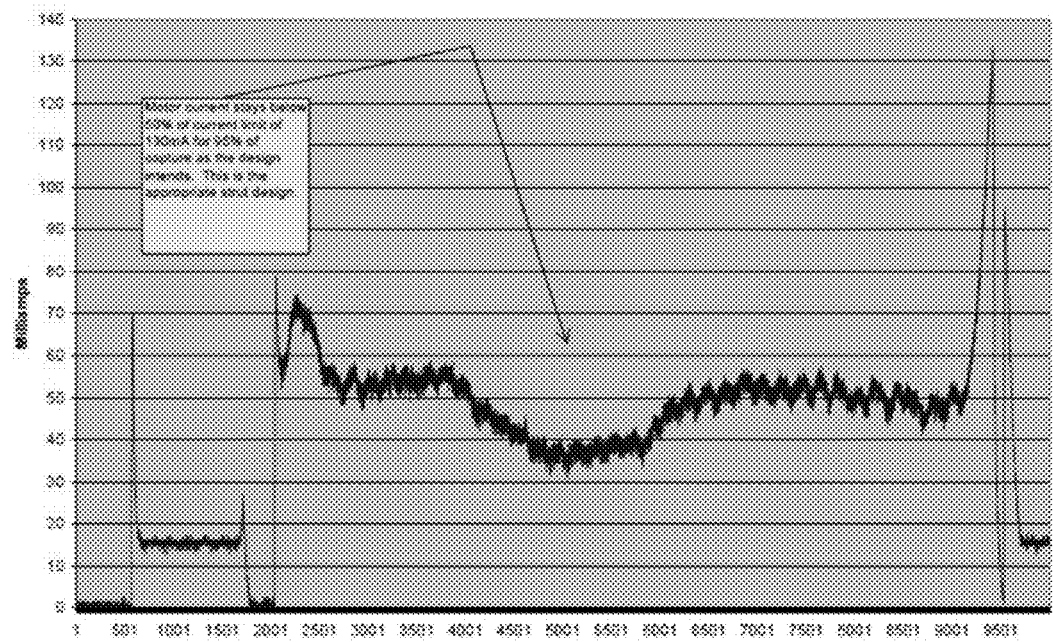

FIG. 38 illustrates a motor current draw of the electrosurgical device exemplified herein. During testing, it was observed that the motor current stayed below 50% of the current limit (of about 130 mA) for much of the capture (about 95%) as desired. FIG. 37 illustrates motor current draw of electrosurgical devices with alternative capture component design, which resulted in higher motor current draw.

Operation

FIG. 36 is diagram of a method 400 of operating an electrosurgical instrument according to an illustrative embodiment. The method 400 includes providing an electrosurgical instrument having one or more electrosurgical filaments (e.g., tungsten alloy filaments) and a plurality of capture components (e.g., elongated stainless-steel leafs) coupled, at their leading edges, to the electrosurgical filaments to define a cutting plane. In particular, the method includes providing an electrosurgical instrument having capture components with varying stiffness along their length of extension (step 402).

The method 400 includes energizing the one or more electrosurgical filaments with high frequency electrical energy, e.g., by a power generator. More particularly, one or more electrosurgical filaments coupled to leading edges of the capture components to form a cutting plane are energized with high frequency electrical energy by a power generator (step 404). The power generator, in some embodiments, generates electric waveform greater than 100 KHz, e.g., at about 340 KHz. A closed feedback control loop regulates the power output to the electrosurgical filaments to maintain a uniform power density along the filaments. In some implementations, the power generator generates a first waveform to initiate an electric cutting arc and then transitions the controls of the electric output to a defined cutting power level.

The method 400 includes extending each of the plurality of capture components and the electrosurgical filaments by forward extension at or near a forward tip of an elongated shaft of the apparatus to form an elliptical path. The combined elliptical path of the capture components and electrosurgical filaments form a spheroidal receptacle to surround a tissue volume for resection (step 406).

Example Electrosurgical System

FIG. 15 illustrates an example electrosurgical system 10 with a capture instrument. In some embodiments, the system 10 includes a capture instrument 12 that includes a reusable component 14 (sometimes referred to as a "handle") and a disposable delivery component 16 (sometimes referred to as a "probe"), which is removably mounted within the polymeric housing 18 of reusable component 14. In some embodiments, the handle 14 and delivery component 16 are integrated as a single disposable unit.

In some embodiments, the delivery component 16 includes an elongate cannula assembly 22, which extends along and is symmetrically disposed about an instrument axis 24. The proximal portion of cannula assembly 22 extends, in some embodiments, through a rotatable, externally threaded connector 26. Connector 26, in turn, is threadably engaged within housing 18. Cannula assembly 22 additionally extends, in some embodiments, through a rotatable suction manifold 28 which is a component of an evacuation system. Manifold 28 is retained, in some embodiments, in position on the cannula assembly 22 by a ferrule or collar 30 which is mounted over the exterior or outward surface of a tubular cannula component 32. The forward region 34 of the cannula assembly 22 extends, in some embodiments, to a distal end or tip 36.

In some embodiments, suction or vacuum manifold 28 is in vacuum conveying and fluid receiving relationship through cannula assembly 22, e.g., with four intake ports, located at forward region 34, two of which are shown at 38. A thermally insulative sleeve 4218 (FIG. 29) is positioned, in some embodiments, over cannula component 32 to protect patient tissue from thermal damage. In some embodiments, vacuum is conveyed to and this elevated temperature fluid is received from suction manifold 28 via a flexible transparent polymeric tube 40. In some embodiments, tube 40 extends from an evacuation outlet at manifold 28 into press-fit connection with a connector 42 and a connector 44, whereupon it is coupled with a flexible tube 46 or hose of larger diametric extent. In some embodiments, hose 46 extends to a fluid trap and filter assemblage 48 which is in vacuum communication via flexible hose 50 with the suction 30 input of a suction pump assembly 52. Pump assembly 52 may be actuated into operation from a switch arrangement shown at 54 or through the utilization of a footswitch 56 coupled to the pump assembly 52 via a cable 58.

In some embodiments, positioned at the forward portion of housing 18 are, e.g., three button switches 62-64 which function respectively as an arm/disarm switch; an energize/position switch; and a start tissue capture switch. In some embodiments, immediately above the switches 62-64 on each side of housing 18 are linear arrays 66 of light emitting diode (LED) based indicator or cueing lights (e.g., provide a start/reset cue; a tissue capture complete cue; a start tissue capture cue; an energize/position cue; and an arm/disarm cue).

In some embodiments, energization and electrical control is provided to the instrument 12 via a multi-lead cable 68 which connects with a combined control assembly and electrosurgical generator 70 and incorporated within a console 72. In some embodiments, the control assembly function performs in conjunction with control assembly counterparts incorporated within instrument 12 and principally within reusable component 14. In some embodiments, connection of the cable 68 with the console 72 includes a multi-lead connector 74 which is coupled to a console connector 76. In some embodiments, the electro-surgically active electrode assembly of the instrument 12 performs in mono polar fashion. Thus, in such embodiments, a conventional, relatively large dispersive return electrode assembly 80 is positioned against the skin surface of the patient. In some embodiments, assembly 80 is configured as having two electrode components 82 and 84 which are connected via cable 86 and connector 88 to console connector 90. In some embodiments, power is supplied to the circuitry at console 72 upon actuation of an on/off switch 92. In some embodiments, when switch 92 is in an "on" orientation, a green visual indicator LED 94 located above the switch is energized. In some embodiments, proper connection of the cable 68 and connector 74 with console connector 76 is indicated by an illuminated green LED 96 positioned above connector 76. In some embodiments, this connection test is carried out by directing current to a coding resistor within housing 18. In some embodiments, a three-pedal foot switch 15 represented generally at 98 is coupled via a cable 100 to the rear panel of console 72. The three-pedals, 98a, 98b, and 98c of switch 98 emulate and provides alternative switching with respect to button switches 62-64.

In some embodiments, visual cueing corresponding with that at housing 18 LED arrays 66 also is provided at console 72. In this regard, a start/reset switch 102 is operationally associated with an LED indicator 104 which illuminates in a green color upon actuation of that switch. In some embodiments, an energize/position mode visual cue LED 106 represents an energization of a precursor electrode assembly at tip 36. This LED provides a yellow output during the electrosurgical advancement of cannula assembly tip 36 into confronting adjacency with a targeted tissue volume. It should be noted that the electrosurgical implementation of the precursor assembly represents one approach. However, in some embodiments, an electrically insulative precursor blade as well as trocar assembly may be provided.

As a next visual cueing, a green, arm/capture mode visual cue is provided, in some embodiments, by an LED 108 to represent an arming of the tissue capture feature of instrument 12. In some embodiments, once an arm/disarm switch 62 or 98a is depressed, the energize/position switches 63 or 98b are no longer activatable. However, in some embodiments, the practitioner can return to the positioning mode by again depressing an arm/disarm switch. To enter a capture mode, in some embodiments, the practitioner depresses the foot switch 98c or capture switch 64. A yellow capture mode visual cue is provided, in some embodiments, by an LED 110 to represent the start of and carrying out of a tissue capture or retrieval procedure and upon completion of such capture, a green capture complete visual cue is provided by a green LED 112. A pause mode condition is represented, in some embodiments, by the energization of a green LED 114. In general, the pause mode is entered, in some embodiments, during a procedure by releasing capture switch 64 or foot switch 98c. In such embodiments, when in a pause mode, the active capture electrodes of the instrument 12 are not energized and deployment of its capture component is halted. However, in some embodiments, the evacuation function carried out by the suction pump assembly 52 continues to perform. To reenter the capture mode, in some embodiments, the practitioner again depresses foot switch 98c or capture switch 64. Upon such re-actuation of the chosen switch, the capture mode continues, in effect, from the orientation where it left off. This pause mode of operation of the system may be employed by the practitioner during a capture mode of operation to permit, for example, the evacuation of fluids encountered by arc-based cutting components. Such fluids may, for example, be accumulations of local anesthetic solution, blood or the like.

In some embodiments, an assurance that the vacuum system is operating, at least to the extent that the vacuum pump assembly 52 is active, is accomplished with a vacuum actuated switch (not shown) attached with the conduit extending between the pump assembly 52 and the instrument 12. For example, unless such a switch is actuated, the commencement of a procedure can be logically blocked by the control assembly 70. In addition to the removal of smoke and such fluids as are discussed above, in some embodiments, the evacuation system including pump assembly 52, conduit defining a transfer channel extending to the intake ports 38, functions to remove steam which is generated by the encounter of an electro surgical cutting arc with fluid of tissue cells. This removal of steam (as a component of elevated temperature fluid) serves, inter alia, to protect healthy tissue surrounding the region of cutting from thermal trauma. In some embodiments, at the time the connector 88 of return electrode 80 is coupled to console connector 90 and switch 92 is in a "power on" condition, a patient circuit safety monitor (PCSM) carries out a self-test. In some embodiments, on subsequent actuation of the start/reset switch 102, a fault test with respect to the two electrode components 82 and 84 is performed. In some embodiments, in the event the latter test fails, then both visual and aural pulsating warning cues re-activated, the visual cue being provided at a red LED 122 located adjacent connector 90.

Delivery Component of the Handheld Instrument

Referring to FIG. 16, the delivery component 16 of the handheld instrument 12 is revealed in an orientation prior to its insertion within the housing 18 of reusable component 14. In the figure, cannula assembly 22 is seen extending forwardly from a cylindrically-shaped support housing 130. In some embodiments, the forward region of the support housing 130 supports the rotatable connector 26. In this regard, it may be observed that the connector 26 is configured with external threads 132 which are affixed for rotation with a grasping surface 134 formed with spaced indentations to facilitate its hand rotation. At the rearward end of support housing 130, in some embodiments, there is located an upstanding indexing pin 136 which, during installation of the disposable component 16, is slidably received within an upwardly disposed elongate slot 138 extending internally along an elongate receiving cavity 140. The forward end of receiving cavity 140 of housing 18 is formed, in some embodiments, with an alignment bushing 128. In some embodiments, alignment bushing 128 is configured with internal threads 142. In some embodiments, internal threads 142 of alignment bushing 128 within cavity 140 threadably engage the external threads 132 of connector 26 when the disposable component 16 is mounted with the reusable component 14.

In some embodiments, positioned opposite indexing pin 136 on support housing 130 are two, spaced apart electrical contacts 146 and 148 which are oriented to make wiping contact with corresponding electrical terminals disposed within housing 18 upon the insertion of support housing within the receiving cavity 140. In some embodiments, contacts 146 and 148 selectively receive electrosurgical cutting current which is applied respectively to a precursor electrode assembly at tip 36 and the electrosurgical cutting and pursing cables associated with a capture component initially retained within cannula assembly 22. In some embodiments, those pursing cables extend from the capture component within cannula component 32 to a cable terminator component having guidance tabs or ears, one of which is revealed at 150 slidably mounted within an elongate stabilizer slot 152 arranged in parallel with axis 24. In some embodiments, a corresponding guidance tab and slot combination is found at the opposite side of supporting housing 130. In some embodiments, located forwardly of the slots as at 152 are two elongate drive slots, one of which is shown at 156 similarly arranged in parallel with axis 24. In some embodiments, the outwardly extending ears or guide tabs of a drive assembly drive member extend from these slots and are seen at 160 and 162. In some embodiments, these ears or tabs 160 and 162 support rearwardly disposed driven surfaces which are used to impart forward movement to the drive assembly component. In some embodiments, this forward movement functions to deploy the noted capture component from cannula component 32. In some embodiments, when the support housing 130 is installed within the receiving cavity 140 of housing 18, these tabs 160 and 162 pass through oppositely disposed notches shown respectively at 164 and 166 provided at a forward portion of housing 18 as part of alignment bushing 128. Similarly, a notch 168 is located forwardly within housing 18, in some embodiments, to permit passage of the electrical terminal 146 and 148. In some embodiments, alignment bushing 128 is configured to form the forward portion of the elongate slot 138 and notch 168.

In some embodiments, the procedure for installing the disposable component 16 within reusable component 14 involves the sliding of support housing 130 within the receiving cavity 140 and rotating grasping surface 134 of connector 26 to provide for the engagement of threads 132 with threads 142. In some embodiments, upon completing the assembly, the flexible, transparent tube 42 of the evacuation assembly may be attached to an evacuation outlet 170 depending outwardly and in fluid and suction or vacuum communication with suction manifold 28. Finally, in some embodiments, a tab 172 is seen extended through a forward portion of the drive slot 156. This tab may be a component above a drive assembly providing a positive blocking or stop limiting the extent of forward travel permitted by the drive member component having the ears 160 and 162. It is located in accordance with a pre-selected capture component maximum effective diametric extent. When the stop function is carried out, in some embodiments, a capture complete signal is derived as a current spike witnessed upon a stall of an electric drive motor. That signal is conveyed to control assembly 70.

Handle of the Capture Instrument

Figure 29:
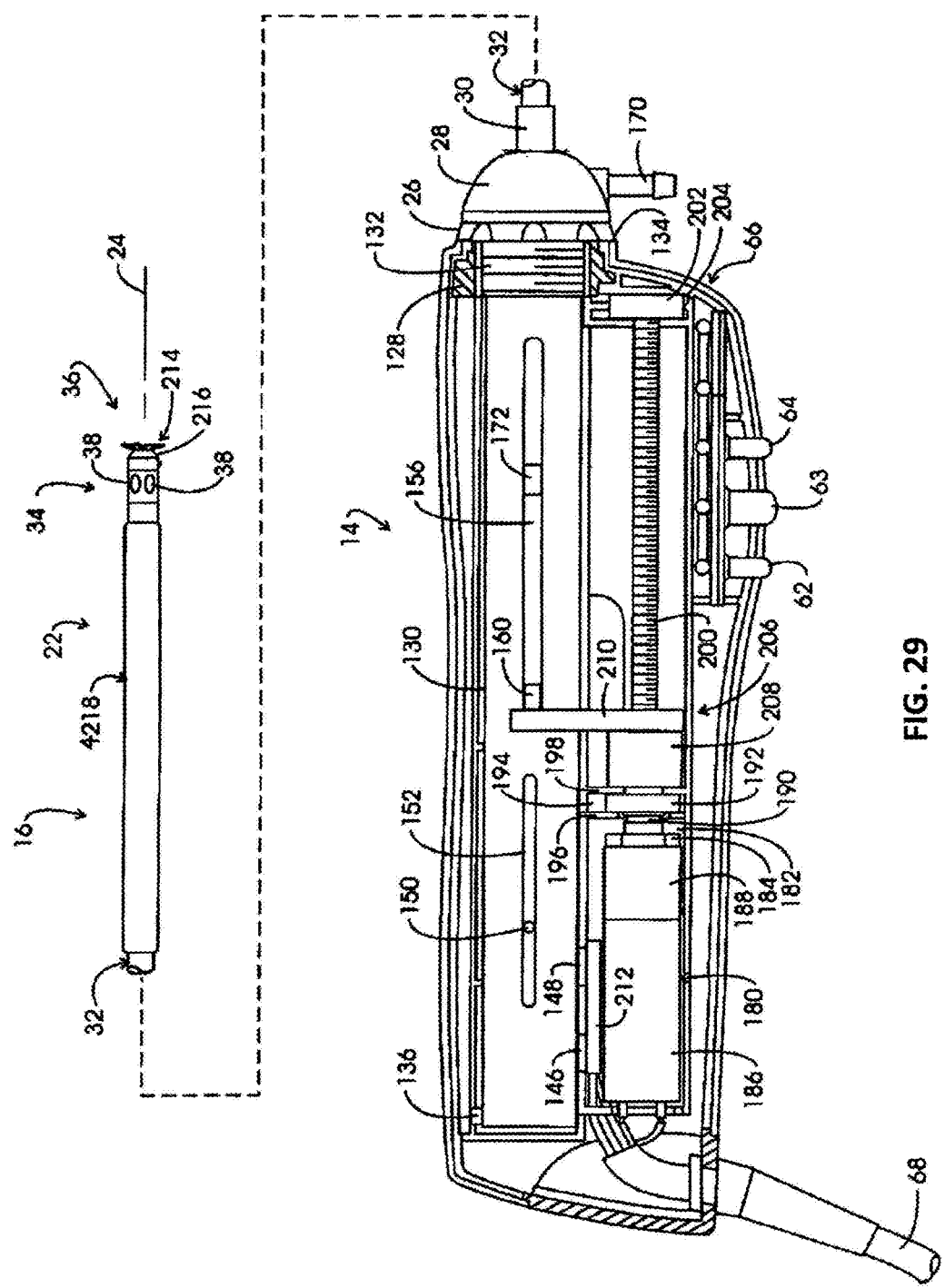
FIG. 29 is a partial sectional view of an example handle component of the electrosurgical instrument shown in FIG. 16 with portions broken away.

Referring to FIG. 29, a sectional view is presented illustrating, in some embodiments, the operative association of motor drive features of the reusable component 14 with the support housing 130 of disposable component 16. In the figure, a motor assembly 180 is seen to be located within a motor mount chamber 182. In some embodiments, in that chamber 182 the motor assembly 180 is permitted some self-aligning movement but is restrained from rotational movement by a torque stop component 184. In some embodiments, assembly 180 incorporates a motor component 186 which is coupled in driving relationship with a planetary gear assembly 188. In some embodiments, the drive output of the planetary gear assembly 188 is connected in driving relationship with a stainless steel flexible bellows-shaped coupler 190 which extends through a fluid seal 192 located within a seal chamber 194 defined by oppositely disposed and spaced apart bulkheads 196 and 198. In some embodiments, seal 192 does not constrain the coupler 190 and permits the noted self-alignment of motor assembly 180 with respect to its coupling to a rearward end of an elongate threaded translation component 200. In some embodiments, the forward end of translation component 200 extends into engagement with a thrust bearing 202. In some embodiments, bearing 202 provides support against all of the driving forces imposed from the motor assembly 180 and is mounted and secured within a thrust bearing chamber 204. In some embodiments, translation component 200 is threadably engaged with a transfer assembly represented generally at 206 which comprises a ball screw or nut component 208 and a generally Y-shaped yoke 210 which is configured to extend to a position aligned for driving but freely abutting engagement with the tabs or ears 160 and 162 (FIG. 16). In some embodiments, during the capture procedure, the translation component 200 is drivably rotated in an appropriate direction to move the transfer assembly 206 forwardly. In some embodiments, that movement, in turn, urges a drive component forwardly until capture component pursing activity is completed and the motor component 186 enters a stall condition. At that juncture, the control system 70 halts, in some embodiments, electrosurgical cutting current and reverses the directional drive sense of motor 186 to cause the transfer assembly 206 to return to a "home" position generally illustrated in the instant figure. The figure additionally reveals, in some embodiments, that the two electrical contacts 146 and 148 located upon support housing 130 will be in contact with corresponding contacts (not shown) supported by a polymeric contact clamp 212.

FIG. 29 also reveals some details of the tip 36 of the cannula assembly 22. In some embodiment, the tip incorporates four straight generally L-shaped precursor electrode components arranged in a cruciform shape or symmetrically about instrument axis 24 as is represented in general at 214. The electrode components of the precursor assembly 214 will be seen to be spaced forwardly of a truncated cone-shaped ceramic (alumina) protective tip component 216. Tip component 216 functions to provide an arc-resistant or arc isolating tip portion preventing its breakdown. For this electrosurgical embodiment of the precursor assembly, the geometry of the electrode components as well as their spacing is selected for the purpose of avoiding arc-over in conjunction with the leading edge of the capture component.

Figure 30:
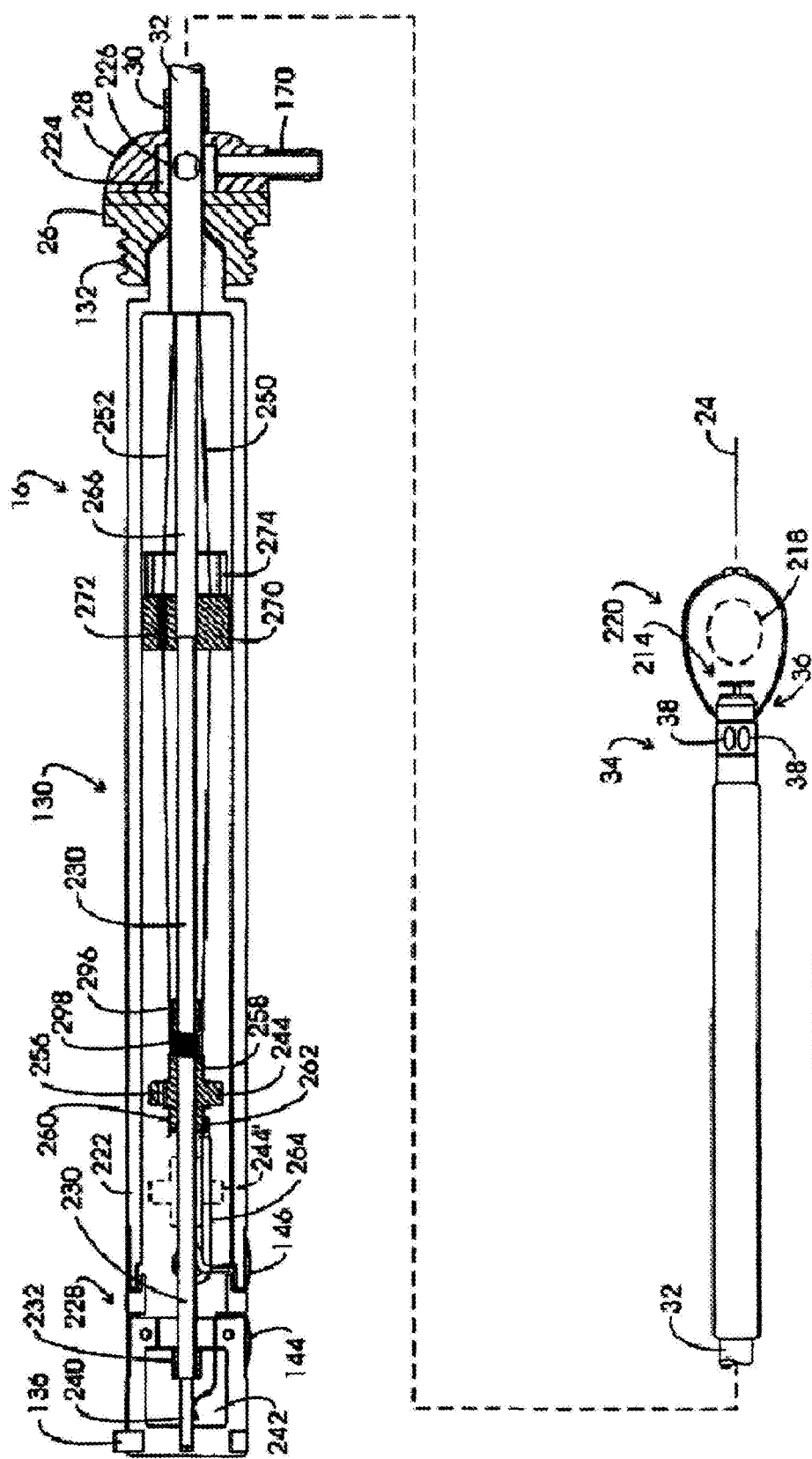
FIG. 30 is a partial sectional view of the example electrosurgical instrument of FIG. 17 showing the orientation of components at a final deployment stage of the capture components.

Referring to FIG. 30, the orientation of the deployment drive components is revealed in connection with a full capture of a target tissue symbolically indicated at 218. The sectional view of support housing 130 shows that it is formed from two identical moldings 222. These paired moldings are retained together, in some embodiments, adhesively as well as forwardly by connector 26 which, additionally supports cannula component 32. Component 32 extends, in some embodiments, through an evacuation chamber 224 formed within manifold 28. In some embodiments, vacuum communication with the chamber 224 is provided by a port or opening 226 in component 32.

Extending from adhesive attachment at a rearward bulkhead 228 defined by the paired molding components is, in some embodiments, the inward portion of a support tube 230. In some embodiments, tube 230 is anchored at the rearward side of bulkhead 228 by a plastic collar 232 and extends forwardly to the forward region 34. In some embodiments, insulatively extending through the interior of the support tube 230 is a precursor electrode tube 240 which is in physical and electrical contact with the precursor assembly 214. In some embodiments, the rear tip of tube 240 extends along axis 24 into engagement with the paired molding components at a cavity 242. In some embodiments, that portion of the precursor electrode tube 240 which extends rearwardly from support tube 230 is configured with an electrically conductive surface which receives precursor electrode current through resiliently biased terminal component 144.

In some embodiments, five braided stainless steel cables extend from their connection with the capture component 220 to a polymeric cable terminator component 244 which is slidably mounted over support tube 230 and is moveable thereon in parallel with the instrument axis 24. In some embodiments, two of the braided pursing cables are stylistically represented in the drawing at 250 and 252. However, all five of these cables extend to and are connected with the cable terminator component 244. Component 244 is formed, in some embodiments, with five longitudinally disposed and radially spaced channels into each of which one of the cables 250-254 extend (see FIGS. 26 and 27). In the figure, cable 252 is seen extending through a channel 256. All five cables are retained or fixed, in some embodiments, to the terminator component 244 by two stainless steel collars. In this regard, a forward stainless steel collar or ferrule is shown at 258 while a rearward one is shown at 260. In some embodiments, collar 260 additionally functions to apply electrosurgical cutting power or current simultaneously to all five of the pursing cables and, accordingly, it initially is nickel plated and then gold plated such that the electrosurgical cutting current may be applied to it through a solder union 262. In some embodiments, union 262 connects the collar 260 with a multi-strand and highly flexible insulated copper cable 264. In some embodiments, cable 264, in turn, is soldered (or welded) to the forward electrical terminal assembly 146. In some embodiments, terminator component 244 is stabilized for slidable movement by two outwardly extending guide tabs or ears, one of which has been described at 148 in conjunction with slot 152 in FIGS. 16 and 29. In some embodiments, with this arrangement, as the five cables are electrically excited with electrosurgical cutting current, they are drawn in tension forwardly to, in turn, pull the terminator component from its initial position shown in phantom at 244' in slidable fashion forwardly over the support tube 230.

In some embodiments, drive is imparted to the five somewhat elongate leafs of capture component 220 from a drive tube 266 which, as described in connection with FIG. 29, is, in turn, driven from its outwardly disposed drive ears or tabs 160 and 162. These tabs extend, in some embodiments, through slots, one of which is shown at 156 in FIG. 29. The drive member associated with these tabs is shown in FIG. 30 at 270 in its capture complete orientation. In some embodiments, member 270 is attached to drive tube 266 which is slidably mounted over support tube 230. In some embodiments, as drive member 270 is driven forwardly from its initial position (not shown), the five pursing cables 250-254 pass through it via five channels. One such channel is stylistically represented in the figure at 272 in connection with cable 252. In some embodiments, these cables additionally slide over a capture stop component 274 which is mounted to the housing 130 paired components. In some embodiments, stop 274 is fixed in place in conjunction with earlier-described tab 172 (FIG. 16). The drive member 270 will have abuttably contacted stop member 274 at the completion of pursing capture as represented in this figure.

Figure 31:
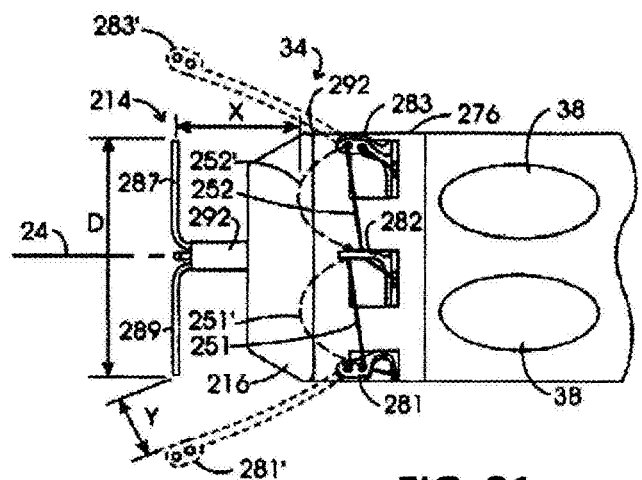
FIG. 31 is a view of the forward region of an example delivery component of the electrosurgical instrument of FIG. 15.

Referring to FIG. 31, an enlarged view of forward region 34, surface 276 and capture component cables 251 and 252 is revealed. In normal usage, the cables as at 251 and 252, in some embodiments, will have the orientation shown in solid line fashion which corresponds with the phantom location 244' of terminator component 244 as seen in FIG. 30. In the course of shipping and/or handling, however, the terminator component as at 244' may slide forwardly slightly and, thus before its use, should be returned to its initial orientation. If it is permitted to slide forwardly, in some embodiments, then the cables have been observed to "slacken" forwardly as shown in FIG. 31 at 251' and 252'. During an energize/position mode described in connection with FIG. 15 in conjunction with foot pedal 98a, switch 63 and LED 106, precursor assembly 214, in some embodiments, will be at a high voltage arc creating condition and the cables as at 251' and 252' will be essentially at ground.

Returning to FIG. 30, as the five cables 250-254 are drawn forwardly while electrically excited, the terminator component 244 will encounter, in some embodiments, cable stop 296 at a location which is selected to establish the maximum effective "diametric extent" of opening as well as the overall length of the containment structure or cage generated by capture component 220. In this regard, that effective diametric extent may range from about 10 mm to about 50 mm. The term "effective" is utilized in connection with diametric extent inasmuch as the profile defined by the cables while excited emulates a pentagon.

In general, cable stop collar 296 is located, in some embodiments, such that the sliding movement of terminator component 244 is blocked when capture component 220 achieves the intermediate position generally representing about one half of its longitudinal deployment at which position the noted maximum effective diametric extent is realized. That maximum effective diametric extent is represented schematically in FIG. 28B and is further represented in FIG. 27 where the pentagon emulation may be observed. The capturing performance of instrument 12 may be improved, in some embodiments, such that its use may extend to the recovery of very dense tissue by deriving a pursing stress on the cables which progressively increases toward a higher value generally established by blockage at cable stop 296. This progressive cable loading occurs, in some embodiments, as the terminator component 244 approaches stop 296 and, looking to FIG. 30, is implemented by the positioning of a resilient component present as a compression spring 298 located in abutment with cable stop collar 296. With the arrangement, the elliptical compression spring functions to modulate the extent of tension applied to the cable such that the leaf tip regions are more gradually vectored inwardly toward axis 24 at the commencement of pursing activity. A more detailed description of the performance of spring 298 and the capture component 220 is provided in application for U.S. patent Ser. No. 10/630,336 entitled "Electrosurgical Method and Apparatus With Dense Tissue Recovery Capacity", by Philip E. Eggers, now U.S. Pat. No. 6,955,653, issued 18 Oct. 2005 the contents of which are incorporated by reference herein in their entirety. In some embodiments, energization of motor assembly 180 continues until drive member 270 abuttably engages capture stop component 274 (FIG. 30). In some embodiments, at that point in time, a resultant inductive spike is created which shuts down electrosurgical excitation of cables 250-254 and causes the motor assembly 180 to reverse and return yoke

210 (FIG. 29) to its "home" position. In some embodiments, capture component 220 will have been maneuvered at pursing angles of attack until the noted de-energization of motor assembly 180 to assume a profile symbolically represented in FIGS. 30 and 28C.

In some embodiments, a surgically sharpened mechanical tip for the positioning of the sampling instrument with respect to a target tissue volume is employed. Mechanical, surgically sharp precursor assemblies may be employed with systems as at 10, however, to avoid arc-over phenomena, these mechanical tips should be not only sharp, but electrically insulative. Ceramic blades, in particular, formed of a zirconia (e.g., those marketed by Specialty Blades, Inc. of Staunton, Va.), may be employed.

Figure 34:
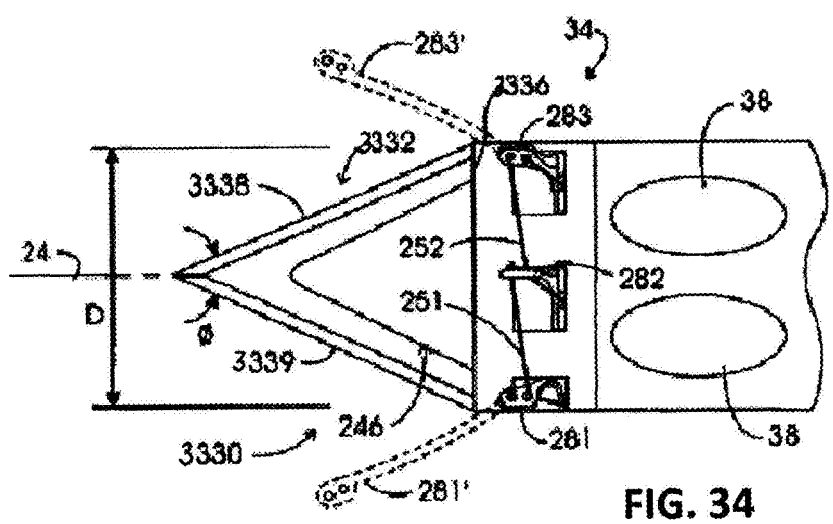
FIG. 34 is a partial view of the forward region of the electrosurgical instrument of FIG. 15 in combination with a blade type precursor.

Looking to FIG. 34, instrument forward region 34 is reproduced in the manner of FIG. 31 with the same identifying numeration. However, for the arrangement of this figure the alumina tip component 216 as shown in FIG. 31 has been removed and thus the blade 3332 base 3336 is located further axially inwardly with respect to the capture component leads and cables.

Figure 32:
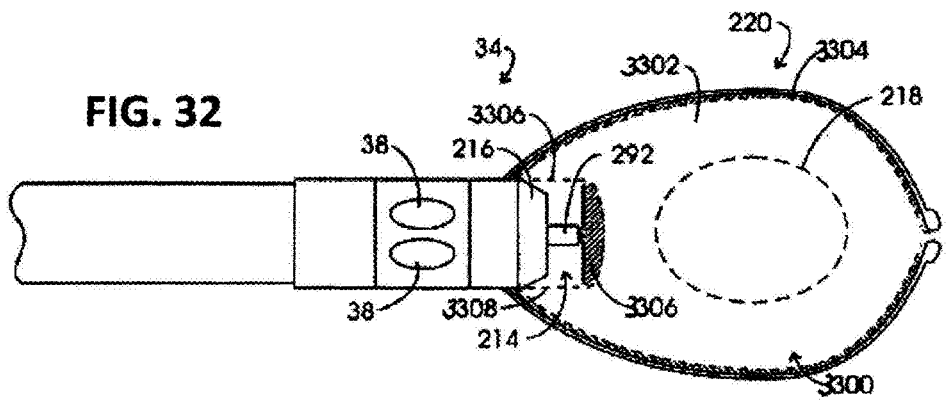
FIG. 32 is a side view of the forward region of the electrosurgical instrument of FIG. 15 showing artifact regions.
Figure 33:
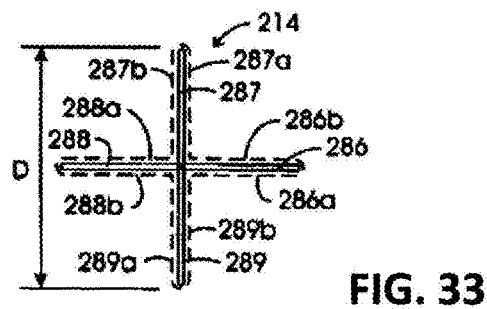
FIG. 33 is a front view of a cruciform type precursor electrode.
Figure 35:
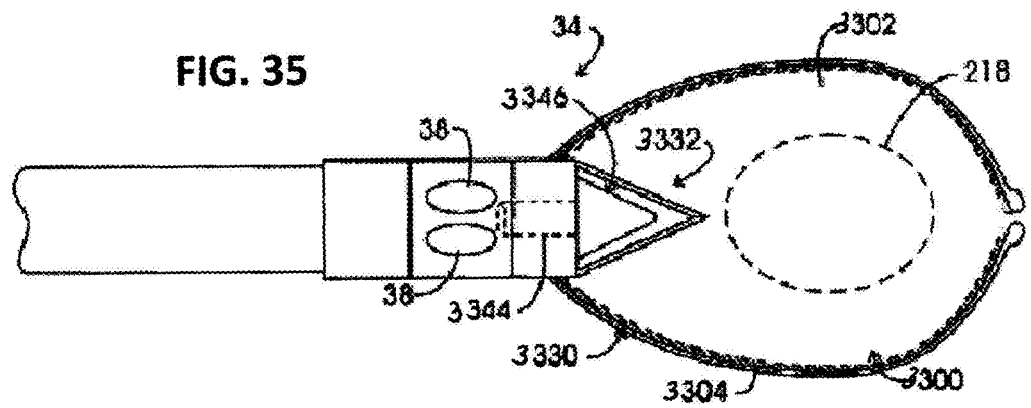
FIG. 35 is a view of the forward region of the electrosurgical instrument of FIG. 34.

Looking to FIG. 35, tip region 34 is presented in the manner of FIG. 32, again with the removal of alumina tip component 216 and electrosurgical precursor assembly 214. The relative orientation of surgical blade 3332 is illustrated with respect to target tissue volume 218. Biopsy or excised sample 3300 is seen to exhibit the same peripheral thermal artifact 3304 which is of no pathology moment and no zone of artifact associated with the precursor assembly is present.

Preferably, blade edges as at 3338 and 3339 will equal or approach, in some embodiments, the Bard-Parker gold standard of sharpness. In general, the value of, D, will be in a range from about 3 mm to about 10 mm, in some embodiments, and preferably within a range of from about 5 mm to about 7 mm. This base width also applies to trocar-type tips. Also, the included angle, $\varphi$, will be in a range of from about 30° to about 70° and preferably within a range of from about 40° to about 55°.

Examples of electrosurgical systems and components that can be used with the capture devices described herein include those described in the following U.S. patents and patent applications, the contents of which are all incorporated by reference in their entirety: U.S. Pat. No. 7,569,053, titled, "Apparatus for retrieving a tissue volume with improved positioning precursor assembly," by Eggers et al.; U.S. Pat. No. 7,494,473, titled, "Electrical apparatus and system with improved tissue capture component," by Eggers et al.; U.S. Pat. No. 6,955,653, titled, "Electrosurgical method and apparatus with dense tissue recovery capacity," by Eggers, Philip; U.S. Pat. No. 6,923,809, titled, "Minimally invasive instrumentation for recovering tissue," by Eggers et al.; U.S. Pat. No. 7,004,174, titled, "Electrosurgery with infiltration anesthesia," by Eggers et al.; U.S. Application 2005/0267455, titled, "Electrosurgery with infiltration anesthesia," by Eggers et al.; and U.S. Pat. No. 7,828,707, titled, "Electrosurgical accessing of tissue with controlled collateral thermal phenomena," by Eggers, Phillip.

Computing Device

In some embodiments, the console 72 may include a computing device having a processor, a memory, a storage device, a high-speed interface connecting to the memory and multiple high-speed expansion ports, and a low-speed interface connecting to a low-speed expansion port and the storage device. Each of the processor, the memory, the storage device, the high-speed interface, the high-speed expansion ports, and the low-speed interface, are interconnected using various busses, and may be mounted on a common motherboard or in other manners as appropriate. The processor can process instructions for execution within the computing device, including instructions stored in the memory or on the storage device to display graphical information for a GUI on an external input/output device, such as a display coupled to the high-speed interface. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory stores information within the computing device. In some implementations, the memory is a volatile memory unit or units. In some implementations, the memory is a non-volatile memory unit or units. The memory may also be another form of computer-readable medium, such as a magnetic or optical disk.

The storage device is capable of providing mass storage for the computing device. In some implementations, the storage device may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor), perform one or more methods, such as those described above. The instructions can also be stored by one or more storage devices such as computer- or machine readable mediums (for example, the memory, the storage device, or memory on the processor).

The high-speed interface manages bandwidth-intensive operations for the computing device, while the low-speed interface manages lower bandwidth-intensive operations. Such allocation of functions is an example only. In some implementations, the high speed interface is coupled to the memory, the display (e.g., through a graphics processor or accelerator), and to the high-speed expansion ports, which may accept various expansion cards (not shown). In the implementation, the low-speed interface is coupled to the storage device and the low-speed expansion port. The low-speed expansion port, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

While the invention has been particularly shown and described with reference to specific preferred embodiments, it should be understood by those skilled in the art that various changes in form and detail may be made therein without departing from the spirit and scope of the invention as defined by the appended claims.

While the invention has been particularly shown and described with reference to specific preferred embodiments, it should be understood by those skilled in the art that various changes in form and detail may be made therein without departing from the spirit and scope of the disclosure as defined by the appended claims.

It is contemplated that methods, systems, and processes described herein encompass variations and adaptations developed using information from the embodiments described herein.

Throughout the description, where systems and compositions are described as having, including, or comprising specific components, or where processes and methods are described as having, including, or comprising specific steps, it is contemplated that, additionally, there are systems and compositions of the present embodiment that consist essentially of, or consist of, the recited components, and that there are processes and methods of the present embodiment that consist essentially of, or consist of, the recited processing steps.

The mention herein of any publication, for example, in the Background section (or elsewhere), is not an admission that the publication serves as prior art with respect to any of the claims presented herein. The Background section is presented for purposes of clarity and is not meant as a description of prior art with respect to any claim.

Headers are used herein to aid the reader and are not meant to limit the interpretation of the subject matter described.

What is claimed is:

1. An electrosurgical apparatus for cutting and resecting a tissue volume, the apparatus comprising:
one or more electrosurgical filaments; and
a plurality of capture components coupled, at leading edges of the components, to the one or more electrosurgical filaments to define a cutting plane, the plurality of capture components and one or more electrosurgical filaments being deployable by forward extension at or near a forward tip of an elongated shaft of the apparatus to form an elliptical path that defines, with the other capture components, a spheroidal receptacle configured to surround a tissue volume for resection,
wherein the elliptical path is formable by a first extension followed by a second extension, said first extension corresponding to a forward section of the plurality of capture components and having a first axial component and a radial expansion component, and said second extension corresponding to a middle section of the plurality of capture components and having a second axial component and a radial contraction component,
wherein at least one of the plurality of capture components is of varying stiffness, including i) a first stiffness corresponding to the first extension and ii) a second stiffness corresponding to the second extension, wherein the first stiffness is greater than the second stiffness.

2. The apparatus of claim 1,
wherein the first extension corresponds to a first width section of a capture component of the plurality of capture components, and the second extension corresponds to a second width section of the capture component of the plurality of capture components, wherein the first width section has a first width and the second width section has a second width, and wherein the first width is greater than the second width.

3. The apparatus of claim 2, wherein a part of the second width section forms a concave shape.

4. The apparatus of claim 2, wherein a part of the first width section has uniform width.

5. The apparatus of claim 1, wherein the first extension, having the first axial component and the radial expansion component, results from the plurality of capture components and one or more electrosurgical filaments being extendable at the same travel rate.

6. The apparatus of claim 1, wherein the second extension, having the second axial component and the radial contraction component, results from i) the plurality of capture components being extendable at a first travel rate and the one or more electrosurgical filaments being extendable at a second travel rate, the first travel rate being greater than the second travel rate.

7. The apparatus of claim 2, wherein the first width section is at least 0.550 inch in length.

8. The apparatus of claim 1, wherein each of the plurality of capture components is at least 0.004 inch thick.

9. The apparatus of claim 1, wherein the second extension, having the second axial component and the radial contraction component, forms a maximum capture diameter of the apparatus.

10. The apparatus of claim 9, wherein the maximum capture diameter is about 30 millimeters.

11. The apparatus of claim 9, wherein the maximum capture diameter is greater than 30 millimeters.

12. The apparatus of claim 9, wherein the maximum capture diameter is selected from the group consisting of about 10 millimeters, about 12 millimeters, about 15 millimeters, and about 20 millimeters.

13. The apparatus of claim 1, wherein the plurality of capture components are connected together via a base as a single structure.

14. The apparatus of claim 1, each of the plurality of capture components couples to a electrosurgical filament of the one or more electrosurgical filaments via an eyelet, the eyelet comprising a low-friction coating.

15. A method for electrosurgical cutting and resecting of a tissue volume, the method comprising:
providing an electrosurgical instrument comprising:
one or more electrosurgical filaments and
a plurality of capture components coupled, at leading edges of the components, to the one or more electrosurgical filaments to define a cutting plane;
energizing the one or more electrosurgical filaments with high frequency electrical energy; and
extending each of the plurality of capture components and the one or more electrosurgical filaments by forward extension at or near a forward tip of an elongated shaft of the apparatus to form an elliptical path that defines, with the other capture components, a spheroidal receptacle configured to surround a tissue volume for resection, wherein the elliptical path is formable by a first extension followed by a second extension, said first extension corresponding to a forward section of the plurality of capture components and having a first axial component and a radial expansion component, and said second extension corresponding to a middle section of the plurality of capture components and having a second axial component and a radial contraction component, wherein at least one of the plurality of capture components is of varying stiffness, including i) a first stiffness corresponding to the first extension and ii) a second stiffness corresponding to the second extension, wherein the first stiffness is greater than the second stiffness.

16. The method of claim 15,
wherein the first extension corresponds to a first width section of a capture component of the plurality of capture components, and the second extension corresponds to a second width section of the capture component of the plurality of capture components, wherein the first width section has a first width and the second width section has a second width, and wherein the first width is greater than the second width.

17. The method of claim 16, wherein a part of the first width section has uniform width.

18. The method of claim 15, wherein the first extension, having the first axial component and the radial expansion component, results from the plurality of capture components and one or more electrosurgical filaments being extendable at the same travel rate.

19. The method of claim 15, wherein the second extension, having the second axial component and the radial contraction component, results from i) the plurality of capture components being extendable at a first travel rate and the one or more electrosurgical filaments being extendable at a second travel rate, the first travel rate being greater than the second travel rate.

20. The method of claim 16, wherein the first width section is at least 0.550 inch in length.

21. The method of claim 15, wherein each of the plurality of capture components is at least 0.004 inch thick.

22. The method of claim 15, wherein the second extension, having the second axial component and the radial contraction component, forms a maximum capture diameter of the apparatus.

23. The method of claim 22, wherein the maximum capture diameter is about 30 millimeters.

24. The method of claim 22, wherein the maximum capture diameter is greater than 30 millimeters.

25. The method of claim 22, wherein the maximum capture diameter is selected from the group consisting of about 10 millimeters, about 12 millimeters, about 15 millimeters, and about 20 millimeters.

26. The method of claim 15, wherein the plurality capture components are connected together via a base as a single structure.

27. The method of claim 15, each of the plurality of capture components couples to a electrosurgical filament of the one or more electrosurgical filaments via an eyelet, the eyelet comprising a low-friction coating.

28. The method of claim 15, wherein a part of the second width section forms a concave shape.

29. An electrosurgical apparatus comprising:
one or more electrosurgical filaments; and
a plurality of capture components coupled, at leading edges of the components, to the one or more electrosurgical filaments to define a cutting plane, the plurality of capture components and one or more electrosurgical filaments being deployable by forward extension at or near a forward tip of an elongated shaft of the apparatus to form an elliptical path that defines, with the other capture components, a spheroidal receptacle configured to surround a tissue volume for resection,
wherein the elliptical path is formable by a first extension followed by a second extension, said first extension corresponding to a forward section of the plurality of capture components and having a first axial component and a radial expansion component, and said second extension corresponding to a middle section of the plurality of capture components and having a second axial component and a radial contraction component, and wherein the second extension comprises a portion of one or more concave regions.

30. The electrosurgical apparatus of claim 29, wherein the concave regions define an hourglass shape member for each of the plurality of capture components.

* * * * *